(12) United States Patent
Andrecka et al.

(10) Patent No.: US 12,298,241 B2
(45) Date of Patent: May 13, 2025

(54) METHOD OF DETERMINING LIPOPROTEIN CONCENTRATION IN SOLUTION USING LIGHT SCATTERING

(71) Applicant: Oxford University Innovation Limited, Oxfordshire (GB)

(72) Inventors: Joanna Andrecka, Oxford (GB); Philipp Kukura, Oxford (GB); Gavin Young, Oxford (GB); Justin Benesch, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 416 days.

(21) Appl. No.: 16/769,918

(22) PCT Filed: Dec. 4, 2018

(86) PCT No.: PCT/GB2018/053508
§ 371 (c)(1),
(2) Date: Jun. 4, 2020

(87) PCT Pub. No.: WO2019/110977
PCT Pub. Date: Jun. 13, 2019

(65) Prior Publication Data
US 2020/0378891 A1   Dec. 3, 2020

(30) Foreign Application Priority Data

Dec. 4, 2017 (GB) .................... 1720162

(51) Int. Cl.
*G01N 21/49* (2006.01)
*G01N 15/0205* (2024.01)
(Continued)

(52) U.S. Cl.
CPC ......... *G01N 21/49* (2013.01); *G01N 15/0205* (2013.01); *G01N 15/06* (2013.01);
(Continued)

(58) Field of Classification Search
CPC ...... G01B 11/0608; G01B 11/14; G01B 11/28
See application file for complete search history.

(56) References Cited

U.S. PATENT DOCUMENTS 4,039,285 A * 8/1977 Teipel .................... G01N 33/92
436/13
4,211,530 A * 7/1980 Goverde ................ G01N 33/92
436/805
(Continued)

FOREIGN PATENT DOCUMENTS

CN      112400024 A *  2/2021  ............. A61B 10/04
EP       1072887 A2     1/2001
(Continued)

OTHER PUBLICATIONS

Kontush, "HDL particle number and size as predictors of cardiovascular disease," Front. Pharmacol. 6:218 (2015) (6 pages).
(Continued)

*Primary Examiner* — Jonathan M Hansen
*Assistant Examiner* — Jarreas Underwood
(74) *Attorney, Agent, or Firm* — Clark & Elbing LLP

(57) ABSTRACT

The invention relates the use of single particle light scattering, preferably interferometric scattering microscopy (also referred to herein as iSCAT), to measure the concentration of a particle in a solution. The invention furthermore relates to the use of light scattering to detect lipoprotein particles in a sample, and to related diagnostic and treatment methods.

21 Claims, 10 Drawing Sheets

(51) Int. Cl.
  *G01N 15/06* (2024.01)
  *G01N 21/51* (2006.01)
  *G01N 33/68* (2006.01)
  *G01N 33/92* (2006.01)

(52) U.S. Cl.
  CPC ......... *G01N 33/6887* (2013.01); *G01N 33/92* (2013.01); *G01N 2021/513* (2013.01); *G01N 2800/32* (2013.01)

(56) References Cited

U.S. PATENT DOCUMENTS

| | | | | |
|---|---|---|---|---|
| 4,347,312 | A | * 8/1982 | Brown | G01N 33/9446 435/7.93 |
| 4,779,451 | A | * 10/1988 | Ezawa | G01N 15/06 73/865.5 |
| 6,514,770 | B1 | * 2/2003 | Sorin | G01N 33/53 435/7.1 |
| 9,921,165 | B2 | * 3/2018 | Bailey | G01N 33/54373 |
| 9,995,688 | B2 | * 6/2018 | Garcia | G01N 33/5304 |
| 10,816,784 | B1 | * 10/2020 | Hantke | G02B 21/361 |
| 11,397,163 | B2 | * 7/2022 | Sandoghdar | G01N 27/44791 |
| 2003/0047688 | A1 | * 3/2003 | Faris | B01L 3/502792 250/432 R |
| 2005/0019842 | A1 | 1/2005 | Prober et al. | |
| 2005/0250094 | A1 | * 11/2005 | Storhoff | B82Y 10/00 435/5 |
| 2005/0255524 | A1 | * 11/2005 | Prober | B82Y 20/00 435/6.12 |
| 2006/0257961 | A1 | * 11/2006 | Apicella | C07K 14/705 435/32 |
| 2008/0014575 | A1 | * 1/2008 | Nelson | G01N 33/54306 435/5 |
| 2008/0050842 | A1 | * 2/2008 | Golovlev | G01N 33/54373 436/525 |
| 2008/0206104 | A1 | * 8/2008 | Prins | G01N 33/54333 324/252 |
| 2010/0087013 | A1 | * 4/2010 | Lieber | G01N 33/551 257/E21.135 |
| 2010/0285989 | A1 | * 11/2010 | Huo | G01N 33/54346 506/9 |
| 2012/0050736 | A1 | 3/2012 | Strong et al. | |
| 2012/0295369 | A1 | 11/2012 | Lofas et al. | |
| 2013/0017556 | A1 | * 1/2013 | Pritchard, Jr. | G01N 33/92 436/501 |
| 2013/0330230 | A1 | * 12/2013 | Uri | G01N 21/553 422/69 |
| 2014/0049775 | A1 | 2/2014 | Kulkarni | |
| 2014/0141529 | A1 | * 5/2014 | Karlsson | G01N 21/553 436/501 |
| 2015/0146205 | A1 | 5/2015 | Kulkarni | |
| 2015/0192574 | A1 | * 7/2015 | Cottier | G01N 33/5302 422/69 |
| 2015/0231236 | A1 | 8/2015 | Pordy et al. | |
| 2015/0313516 | A1 | 11/2015 | Shimizu et al. | |
| 2016/0046988 | A1 | * 2/2016 | Walter | C12Q 1/6837 422/69 |
| 2017/0089892 | A1 | 3/2017 | Aghvanyan et al. | |
| 2017/0307504 | A1 | * 10/2017 | Kulkarni | G01N 1/38 |
| 2018/0275097 | A1 | * 9/2018 | Sandoghdar | G01N 15/1484 |

FOREIGN PATENT DOCUMENTS

| | | | |
|---|---|---|---|
| EP | 2930495 A1 | 10/2015 | |
| GB | 1561574 A | 2/1980 | |
| JP | H03216554 A | * 1/1990 | |
| JP | 2004505231 A | * 8/2000 | |
| JP | 2005-134205 A | 5/2005 | |
| JP | 2006-515420 A | 5/2006 | |
| JP | 2007-525651 A | 9/2007 | |
| JP | 2010-048703 A | 3/2010 | |
| RU | 2613885 C2 | 3/2017 | |
| WO | WO-2004/044232 A1 | 5/2004 | |
| WO | WO-2005/008222 A2 | 1/2005 | |
| WO | WO-2010039247 A2 | * 4/2010 | G01N 33/54393 |
| WO | WO-2011/034678 A1 | 3/2011 | |
| WO | WO-2013/188879 A1 | 12/2013 | |
| WO | WO-2014/087825 A1 | 6/2014 | |
| WO | WO-2016065487 A1 | * 5/2016 | C12Q 1/04 |
| WO | WO-2017/041809 A1 | 3/2017 | |
| WO | WO-2019110691 A1 | * 6/2019 | C12N 15/102 |
| WO | WO-2020160402 A1 | * 8/2020 | G01N 33/57488 |

OTHER PUBLICATIONS

Sacks et al., "Clinical review 163: Cardiovascular endocrinology 4: Low-density lipoprotein size and cardiovascular disease: a reappraisal," J. Clin. Endocrinol. Metab. 88(10):4525-4532 (2003).

International Search Report and Written Opinion for PCT International Application No. PCT/GB2018/053508, mailed Feb. 14, 2019 (17 pages).

Parikh et al., "Lipoprotein concentration, particle number, size and cholesterol efflux capacity are associated with mitochondrial oxidative stress and function in an HIV positive cohort," available in PMC Mar. 1, 2016, published in final edited form as: Atherosclerosis 239(1):50-54 (2015) (15 pages).

Cole et al., "Label-free single-molecule imaging with numerical-aperture-shaped interferometric scattering microscopy," ACS Photonics 4(2):211-216 (Jan. 2017).

Larosa et al., "Intensive lipid lowering with atorvastatin in patients with stable coronary disease," N. Engl. J. Med. 352(14):1425-1435 (Apr. 2005).

Piliarik et al., "Direct optical sensing of single unlabelled proteins and super-resolution imaging of their binding sites," Nat Commun. 5:4495 (2014) (8 pages).

Communication pursuant to Article 94(3) EPC dated Aug. 8, 2024, for European Patent Application No. 18819262.9, Andrecka et al., "Method of Determining Lipoprotein Concentration in Solution Using Light Scattering," filed Dec. 4, 2018 (6 pages).

* cited by examiner

METHOD OF DETERMINING LIPOPROTEIN CONCENTRATION IN SOLUTION USING LIGHT SCATTERING

STATEMENT OF SUPPORT

The research leading to these results has received funding from the European Research Council under the European Union's Seventh Framework Programme (FP7/2007-2013)/ERC grant agreement no. 337757.

FIELD OF THE INVENTION

The invention relates the use of single particle light scattering, preferably interferometric scattering microscopy (also referred to herein as iSCAT), to measure the concentration of a particle in a solution. The particle may be in a simple or complex solution, such as a biological or environmental sample. The invention may be used to determine the absolute concentration of the particle in solution, and this ability provides a means to study the stoichiometric relationships between different particles in solution. As the inventors have already demonstrated, iSCAT also provides a means for robust and accurate detection, mass quantification, imaging and characterisation of particles as small as single molecules, and therefore the ability to also use the same technique for concentration measurements is highly beneficial.

The invention furthermore relates to the use of light scattering, preferably interferometric scattering microscopy (also referred to herein as iSCAT) to detect lipoprotein particles in a sample, and to related diagnostic and treatment methods. The ability of the present methods to measure the concentration of various lipoproteins in solution is of particular interest.

BACKGROUND iSCAT has materialized as a powerful approach to both single particle tracking with unique spatiotemporal resolution and label-free sensitivity down to the single molecule level.

Interferometric scattering microscopy provides information about the relative distribution of particles of different masses in solution, without the requirement to add a label. Adding absolute or relative concentration of a particle provides valuable additional information about the sample that is being analysed, particularly if the solution is a biological or environmental sample.

Prior to earlier work by the present applicants, widespread application of iSCAT has been limited by the requirement for custom-built microscopes, unconventional cameras and complex sample illumination, limiting that capabilities of iSCAT for the robust and accurate detection, imaging and characterisation of particles as small as single molecules. However, improvements to the instrument have been developed, such that this technology has evolved into a powerful means for looking at single objects. An exemplary design of an iSCAT instrument is described in Cole et al ACS Photonics, 2017, 4 (2), pp 211-216 and Arroyo et al. Nat Protocols 2016, 617-633, both herein incorporated by reference. Further details about the instrument are provided in an earlier application by the present applicant, WO2018/011591, herein incorporated by reference.

iSCAT has been described previously for detection of purified single proteins (Cole et al (ACS Photonics, 2017, 4(2), pp 211-216), but the detection and quantification of lipoproteins has not previously been explored, since detection of particles in a complex solution was not thought to be feasible.

Diagnostic assays for cardiovascular disease may include detection of lipoproteins (also described as lipoprotein particles). Various methods for detection of lipoproteins are reviewed in Circulation. 2009 May 5; 119(17): 2396-2404; Curr Opin Lipidol. 2017 June; 28(3):261-266. These methods have disadvantages of being time-consuming, expensive, providing incomplete information on lipoprotein particles and/or having limited application to clinical settings.

SUMMARY OF INVENTION

The present inventors have surprisingly identified that is possible to use single particle light scattering, preferably single particle interferometric scattering microscopy to determine the concentration of a particle in solution. Additionally, the present inventors have unexpectedly illustrated that it is possible to determine the concentration of particles by single particle light scattering (such as by using iSCAT) directly from a biological sample (such as blood or blood plasma) without purification of the particles away from other components, despite the background signal provided by these other components. This has proven to be a particularly useful technique for lipoproteins in biological samples, for example.

The present invention provides a method of measuring the concentration of a particle in solution, comprising contacting the solution with a surface and detecting the binding of said particle to the surface using light scattering.

The light scattering method for detection of the particle binding is preferably iSCAT. The method may preferably be performed using a suitable microscope. The concentration is preferably absolute concentration. The binding of the particle to said surface may be detected or visualised using single particle light scattering.

The present invention provides a method for determining the concentration of a particle in solution comprising contacting said solution with a measuring solution and a surface, and detecting the binding of the particle to said surface using light scattering.

This feature of the invention is particularly useful for situations in which the solution is thought to be concentrated. A volume of the solution containing the particle may be included with a volume of a measuring solution in a sample holder prior to detection of the binding of the particle to a surface. The advantage of this aspect is to ensure that the concentration measured represents the state of the particle in the original, more concentrated solution.

The present invention provides a method for determining the concentration of a particle in solution comprising contacting the solution with a surface in the presence of a calibrant and detecting the binding of the particle to the surface using light scattering.

Therefore, the present invention enables the concentration measurement of a particle in solution by means of detecting the binding rate of said particle to a surface.

Further, the present invention enables absolute concentration measurement of a particle in solution by analysis of the changes or decay in binding rate of the particle to a surface as detected by light scattering over time.

Absolute concentration in solution may be determined by measuring binding events between particles in the sample and a surface, and be calibrated against those observed with samples of particles of known concentrations. The surface may be part of a sample holder. In a sample holder with a high surface to volume ratio the binding of a particle to the surface decreases over time as a function of the remaining number of particles in solution and accessible sites for binding. Initial binding rates for a series of concentrations may be extrapolated from the binding data and used to generate a standard curve allowing for conversion of a measured initial binding rate in the sample to the respective absolute concentration of the particles in solution.

The binding of the particle to the surface may be detected or visualised using light scattering, preferably iSCAT.

Alternatively, concentration in solution may be determined by use of a passivated or activated surface, such that the binding rate of particles can be controlled by controlling the binding activity between the surface and the particle. In this setting, surface activation or passivation can either increase binding affinity and thus the measurement range to lower concentrations, or lower the binding affinity and therefore be able to measure at higher concentrations.

The surface preferably forms part of a sample holder for said solution. Said sample holder may be an element of a light scattering microscope. The sample holder may be a high surface-to-volume chamber.

In order to calculate the concentration, it may be necessary to include correction for diffusion rates. Diffusion rates can be readily calculated based on known properties of the particle, such as mass and shape.

Therefore, the invention provides a method for measuring the concentration of particle a solution, the method comprising:
i) contacting the solution with a surface;
ii) detecting the particle binding to the surface as visualised by light scattering;
iii) repeating the detection step and calculating changes in binding rate and the initial binding rate over time of the particle to the surface;
iv) providing a calibration curve of initial binding rate against concentration based on data from solutions of known particle concentration;
v) using the calibration curve in step (iv) to convert the initial binding rate recorded for the sample in step (iii) to the concentration of the particle in solution.

Preferably, the concentration is absolute concentration.

In some variations, the solution may be pre-treated before or simultaneously with contact to the surface, for example with a measuring solution or calibrant.

The particle in solution may be contacted with a measuring solution and a surface. The advantage of this aspect is to ensure that the concentration measured represents the state of the particle in the original, more concentrated solution.

The measuring solution may be a buffering solution. Generally, the volume of the measuring solution is known in order to enable calculation of dilution effects.

Various techniques may be required to prepare the solution for concentration determination. For example, a volume of the solution may be placed into a sample holder, preferably with a known geometry. This enables the introduction of a volume of a measuring solution (or introduction of the particle solution into the measuring solution), and using dilution behaviour, this allows the detected binding rate of the particle to the surface to be converted to concentration of the particle.

The detection of the binding of the particle to the surface may be taken at one or more different time intervals following the introduction of the measuring solution. If the detection step is repeated after introduction of measuring solution at different time intervals, this will allow for correction for dilution effects, such as dissociation. If the measurements are taken at different time point after addition (and thus dilution) a change in, for example, species distribution if the particle dissociates or clusters at lower concentrations, can be visualised. This approach, therefore, allows a more detailed view of the particle and enables the verification of the concentration measurement.

Alternatively or additionally, the volume of one or both of the solutions (particle or measuring) can be varied, and/or the geometry of the sample holder can be varied. Both allow for correction of dilution effects. If the detection step is repeated in one or more different solution volumes and/or in sample holders of one or more different geometries this can also correct for dilution effects such as dissociation.

Therefore, the invention provides a method for determining the concentration of a particle in solution, the method comprising:
i) contacting the solution with a surface and a volume of measuring solution in a sample holder with a geometry;
ii) detecting the particle binding to the surface as visualised by light scattering;
iii) repeating the detection step and calculating changes in binding rate and the initial binding rate over time of the particle to the surface;
iv) providing a calibration curve of initial binding rate against concentration based on data from solutions of known particle concentration;
v) using the calibration curve in step (iv) to convert the initial binding rate recorded for the sample in step (iii) to the absolute concentration of the particle in solution.

The method may further involve repeating steps (i) to (ii) using one or more of a sample holder of different geometry or using a different volume of measuring solution in order to verify the determined concentration.

Alternatively, particle in solution may be contacted with a surface in the presence of a calibrant.

The calibrant in solution has a pre-determined concentration and mass. Once it is introduced into the particle solution, the detection of the binding rate of the calibrant and the particle to said surface occurs separately but simultaneously. Repeated measurements of both the particle and the calibrant binding to the surface may be taken, allowing for the determination of the initial binding rate for the particle and the initial binding rate for the calibrant. The initial binding rate of the known concentration of calibrant permits the conversion of the initial binding rate of the particle to concentration of said particle. In one embodiment, the calibrant is selected to resemble the particle with respect to its characteristics in binding to the surface. For example, it is desirable to select a calibrant with similar surface properties (e.g. charge, hydrophobicity, hydrophilicity). Such selection allows more precise measurements over a variety of particles. Effectively, the calibrant and the particle should have the same affinity for the surface, and therefore the determination of the binding rate of the known concentration of calibrant permits the conversion of the binding rate of the particle into a concentration.

Therefore, the invention provides a method for measuring the concentration of particle a solution, the method comprising:
i) contacting the solution with a surface in the presence of a calibrant;
ii) detecting the particle binding to the surface as visualised by light scattering;
iii) simultaneously detecting the calibrant binding to the surface as visualised by light scattering;

iv) repeating the detection steps (ii) and (iii) and calculating changes in binding rate and the initial binding rate over time of the particle and the calibrant to the surface;

v) using the initial binding rates calculated in step (iv) for the calibrant to convert the initial binding rate of the particle calculated in step (iv) to concentration of the particle in solution.

It is preferred that the calibrant is of known concentration, and has similar characteristics to the particle, particularly in respect of binding to the surface.

Furthermore, the present inventors have surprisingly identified that is possible to detect lipoprotein particles, which represent heterogeneous mixtures of different biomolecules including various non-protein components, by light scattering, in particular using interferometric scattering microscopy. Single lipoprotein particles are able to be visualised optically. This allows for numbers and size of lipoprotein particles (and of different classes of lipoprotein particles) to be determined directly in a sample. The relative proportions of different lipoprotein particles in a sample can also be determined in a single measurement. The method of detection of the present invention thus provides a rapid and simple means of detecting lipoprotein particles and provides extensive information on the nature and distribution of lipoprotein particles in the sample. The optical detection carried out is also relatively inexpensive and advantageously suited to clinical settings, and avoids complex processing protocols associated with previous methods for detection of lipoproteins.

Additionally, the present inventors have unexpectedly illustrated that it is possible to detect lipoprotein particles by light scattering (such as by using iSCAT) directly from a biological sample (such as blood or blood plasma) without purification of the particles away from other components, despite the background signal provided by these other components.

The method of detection of the invention is advantageously employed in clinical settings for detection of lipoprotein particles from patient samples, to assist diagnosis and treatment of diseases and conditions associated with size and/or number of lipoprotein particles.

The present invention therefore provides a method for detection of lipoprotein particles in a sample, comprising detecting said particles by light scattering, preferably by interferometric scattering microscopy. The invention further provides a method for diagnosing a disease or condition associated with size and/or number of lipoprotein particles in an individual, or for determining the risk that the individual will develop said disease or condition, comprising detecting the size and/or number of lipoprotein particles in a sample from said individual by interferometric scattering microscopy.

The invention additionally provides a method for selecting an individual to whom a substance or composition is to be administered, or to whom a regimen is to be prescribed, wherein said substance or composition or regimen is suitable for treating or preventing a disease or condition associated with size and/or number of lipoprotein particles, comprising detecting the size and/or number of lipoprotein particles in a sample from said individual by a method for detection of the invention, and selecting said patient for said administration or said regimen if the size and/or number of lipoprotein particles detected is indicative of the presence of said disease or condition, or of a risk thereof.

The invention also provides a method of treating or preventing a disease or condition associated with size and/or number of lipoprotein particles in an individual, the method comprising diagnosing or determining risk of said disease or condition in said individual or selecting said individual by a method of the invention, and administering a substance or composition to the individual, or carrying out a regimen thereon, which is effective to treat or prevent said disease or condition in the individual.

The invention further provides a substance or composition for use in a method of treating or preventing a disease or condition associated with size and/or number of lipoprotein particles in an individual, wherein said individual is diagnosed or determined at risk or selected by a method of the invention.

The invention also provides use of a substance or composition in the manufacture of a medicament for treatment of prevention of a disease or condition associated with size and/or number of lipoprotein particles in an individual, wherein said individual is diagnosed or determined at risk or selected by a method of the invention.

BRIEF DESCRIPTION OF FIGURES

FIG. 6 provides single particle histograms for HDL, LDL, and VLDL lipoprotein particles detected by iSCAT from whole blood samples.

DETAILED DESCRIPTION OF INVENTION

Figure 1:
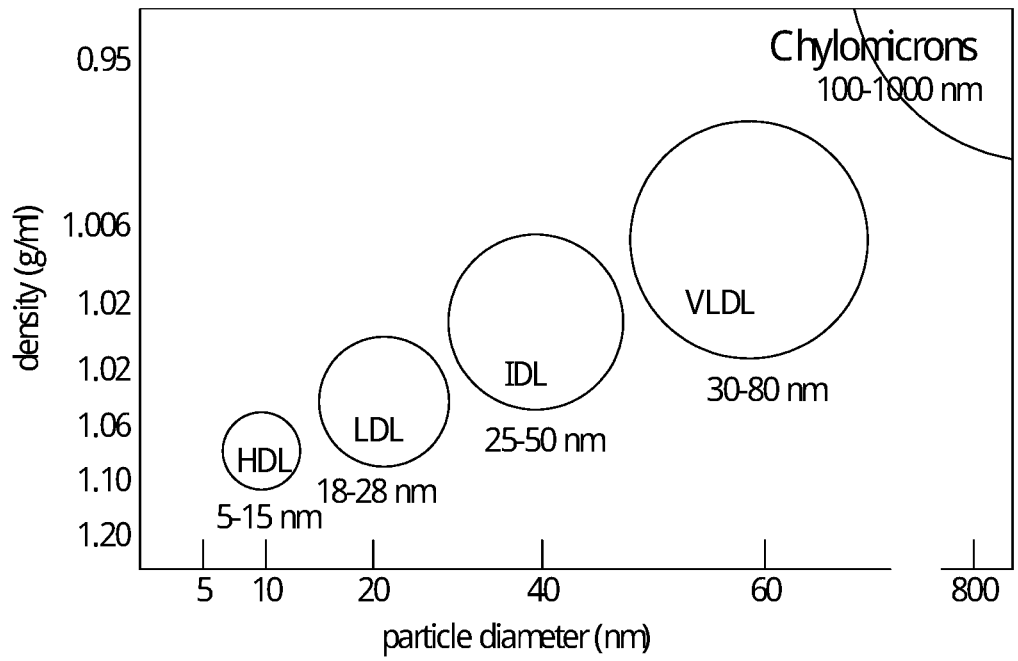
FIG. 1 provides a chart depicting different types of lipoprotein particles present in human blood and their respective diameters (nm) and density (g/ml). The table also provides information on the relative proportions of proteins, cholesterol, phospholipids and triglycerides in each type of particle.
Figure 2:
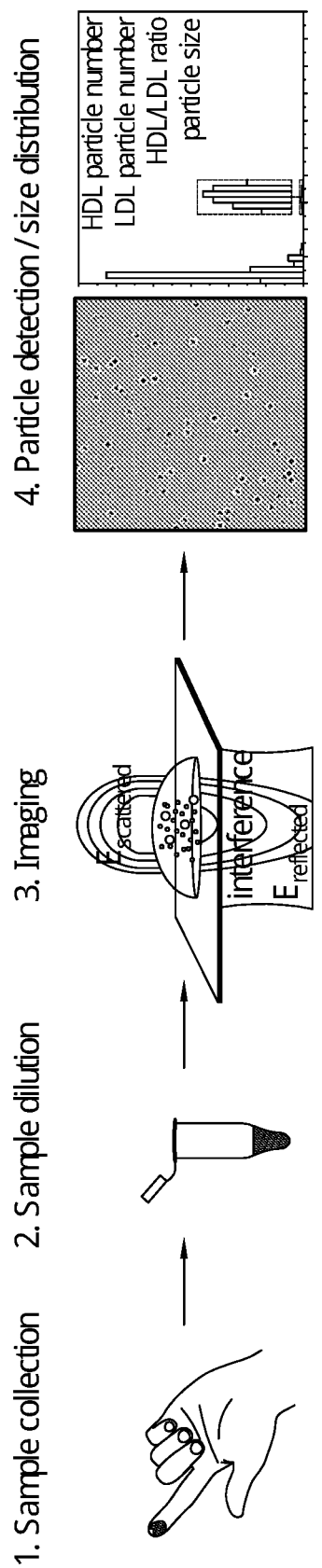
FIG. 2 shows an illustrative scheme for detection of lipoprotein particles by iSCAT from a blood sample.

The present invention enables concentration measurement of a particle in solution by detecting the binding of a particle in a sample to a surface using light scattering. Preferred is the use of a light scattering microscope.

The present inventors have particularly identified the ability to detect single lipoprotein particles directly by light scattering, particularly by use of interferometric scattering microscopy. The invention may be used to detect any form of lipoprotein particle, including different forms of lipoprotein particles in a sample.

Particles

The particle that may be detected according to the methods of the invention may be any particle within a solution, from a single molecule, via biological macromolecules, to an oligomeric assembly. Examples of suitable particles are single molecules, proteins, polypeptides, peptides, amino acids, monosaccharides, carbohydrates, oligosaccharides, polysaccharides, glycopeptides, glycoproteins, lipids, fatty acids, waxes, sterols, fat-soluble vitamins, monoglycerides, diglycerides, triglycerides, phospholipids, glycerolipids, glycerophospholipids, sphingolipids, saccharolipids, polyketides, glycolipids, liopoproteins, nucleic acids, nucleotides, polynucleic acids, clusters of molecules, assemblies, aggregations, protein/protein interactions, protein/small molecule interactions, protein-nucleic acid interactions and/or oligomeric assemblies.

For the determination of concentration of the particles in solution, it is not necessary to label the particle prior to detection. Since the light scattering microscopy is capable of determining the mass of the particle, it can be identified simply by mass.

Lipoprotein Particles

The lipoprotein particles that may be detected according to the invention may be any lipoprotein particles present in a sample. The lipoprotein particles may be of any size or present in any number. The lipoprotein particles are typically selected from lipoprotein particles present in human or animal blood. A lipoprotein particle typically comprises triglycerides, cholesterol, phospholipids and one or more proteins, such as one or more apolipoproteins. Lipoprotein particles may have varying ratios and/or densities of lipids and proteins. An apolipoprotein may be a peripheral or integral apolipoprotein. An apolipoprotein may be selected from any class or sub-class of apolipoproteins. The apolipoprotein may have any genetic polymorphism. The apolipoprotein(s) may be selected from the A, B, C, D, E and/or H classes. Apoliproteins of class A may be selected from apo A-I, apo A-II, apo A-IV, and apo A-V; apolipoproteins of class B may be selected from apo B48 and apo B100); apolipoproteins of class C may be selected from apo C-I, apo C-II, apo C-III, and apo C-IV. Apolipoprotein proteins of class B are found in LDL lipoprotein particles, with apolipoproteins of other classes typically associated with HDL lipoprotein particles.

A lipoprotein particle typically has a diameter of at least 1 nm and may have a diameter of up to 1000 nm or greater. Particular types of lipoprotein particles that may be detected according to the invention include chylomicrons (also described as ultra low density lipoproteins, VLDL), very low-density lipoprotein (VLDL), intermediate low-density lipoprotein (IDL), low-density lipoprotein (LDL), and high-density lipoprotein (HDL). Illustrative particle diameters, densities and lipid:protein ratios for the above lipoprotein particles are provided in FIG. 1. A lipoprotein particle detected in accordance with the invention may have any particle diameter, density or lipid:protein ratio shown in FIG. 1. Thus, for example, an HDL lipoprotein particle may have a particle diameter in the range of about 5 to about 15 nm. An LDL lipoprotein particle may have a particle diameter in the range of about 18 to about 28 nm. An IDL lipoprotein particle may have a particle diameter of about 25 to about 50 nm. A VLDL lipoprotein particle may have a particle diameter of about 30 to about 80 nm. A chylomicron may have a particle diameter of about 100 to about 1000 nm. An HDL lipoprotein particle may have a molecular weight in the range of about 200 to about 500 kDa. An LDL lipoprotein may have a molecular weight of about 3 MDA.

Preferably, the method of the invention detects HDL and/or LDL lipoprotein particles. The method of the invention may comprise detection of VLDL lipoprotein particles. The method of the invention may comprise detection of HDL and LDL; HDL and VLDL; HDL and IDL; HDL and UDL; LDL and VLDL; LDL and IDL; or LDL and UDL lipoprotein particles. The method of the invention may comprise detection of HDL, LDL and VLDL; HDL, LDL and IDL; or HDL, LDL and UDL lipoprotein particles. The method of the invention may comprise detecting HDL, LDL, IDL, VLDL and VLDL lipoprotein particles. Detection of IDL and VLDL particles having an overlapping particle diameter with other types of lipoprotein particles may comprise use of additional steps (such as a fluorescently labelled antibody) to detect specific proteins present in such particles.

Particle in Solution

The solution can be any solution of the particle in a liquid solvent. The solution can be simple, for example the particle dispersed in water (an aqueous solution of the particle) or it can be a complex solution, for example the particle plus one or more other solutes. The solution may be a sample. Samples may be taken from commercially prepared solutions in order to test for concentration. Bodily fluids are examples of complex solutions where numerous solutes are present, including electrolytes, sugar and urea. The sample may be taken from any source, including biological or environmental samples. If the sample is a biological sample, it may be taken or obtained from a human or animal body or individual, for example blood, serum, plasma, urine, saliva, lymph, sweat, amniotic fluid, cerebrospinal fluid, breast milk, tears, secretions, synovial fluid, semen, bile, or mucus. If the sample is an environmental sample, it may be taken from any source, such as water (for example wells, streams, rivers, lakes, rainwater, seawater and the like), food and drinks (for example beverages), agricultural samples or liquid samples from factories and manufacturing processes.

It is not necessary to prepare the solution or sample prior to contacting with the surface, but if the solution is thought to be concentrated, the solution may be contacted with a measuring solution as discussed herein.

Surface

The surface used for binding the particle to determine concentration of the particle is preferably a detector surface and may form part of a sample holder for a light scattering microscope.

The surface is preferably glass, sapphire or made from transparent polymers. The sample is brought into contact with the surface in order to determine concentration. The sample may be placed into a sample holder which includes the surface. As previously described, the microscope comprises a sample holder for holding a sample at a sample location. The sample may be a liquid sample comprising particles to be imaged, which are described in more detail below. The sample holder may take any form suitable for holding the sample. Typically, the sample holder holds the sample on a surface, which forms an interface between the sample holder and the sample. For example, the sample holder may be a coverslip and/or may be made from glass. The sample may be provided on the sample holder in a straightforward manner, for example using a micropipette or an automated dispensing system.

The sample holder may take any appropriate format. In some formats, the sample holder will allow for a high surface area to volume ratio, such that access to the surface does not limit the binding of the particle in the solution. In other formats, the ratio between the surface area and the volume may decrease, such that there is a low surface area to volume ratio, which may limit access of the particles to the surface. It will be clear to those skilled in the art that the selection of surface area to volume of the sample holder will alter the way in which concentration may be measured. If the sample holder has a low surface area to volume ratio, for example, the binding rate of the particle will not decrease over time. In this situation, the binding rate at any moment as detected using light scattering can be used to calculate the concentration.

The surface used in the invention may be any suitable surface. For example, the surface may be a passivated surface. Passivation is the process of treating or coating a surface in order to enhance or reduce the chemical reactivity, thus increasing or decreasing the number of binding events.

Alternatively, the surface may be an activated, coated, derivatised or treated surface. The surface may be derivatised by immobilising an entity to the surface, such as a silane. In Example 4, the surface is coated with APTES, which allows for silanisation, which is the functionalisation of the surfaces with alkoxysilane molecules. This is advantageous for some particles as it leads to a positively charged surface. The coating process with APTES leads to the formation of a covalent bond between the surface and the silane. The protonated amine groups align themselves in the free space and make positive docking sites for the any negatively charged groups (such as sialic acids, carboxyl, and sulphate ester groups) of the particle.

The surface may be coated with a specific binding entity or partner for the particle. Such a surface enables the selection of the particle from concentrated or complex mixtures. The calculation of concentration in this scenario requires the binding constant for the particle and the specific binding entity to be known.

It is important that if the surface is modified that these modifications do not cause any alterations in the ability of the binding of the particle to be detected by light scattering.
Contacting the Sample with a Surface The solution is contacted with the surface in order to determine concentration of a particle in said solution. The particle binds to the surface, and this binding to the surface is visualised or detected using light scattering, preferably iSCAT, and preferably with a microscope.

The binding of the particle to the surface may be non-specific, or alternatively, the binding may be specific, dependent on the nature of the surface used, as discussed above. Should the surface be glass (i.e. a glass coverslip) the binding will be non-specific. Should the surface be treated, the binding may be specific. The rate of binding to the surface may be calculated by repeating the detection step one or more times, or may be taken from a single measurement.

The binding and/or number of particles bound to the surface may be detected using light scattering. This may then be repeated one or more times to determine changes in the binding rate and/or the initial binding rate of the particle to the surface. The binding at each time point may be plotted to establish the binding rate.

In instances where the ratio of the surface area to volume of the solution is low, one measurement may be sufficient in order to determine the concentration, since the binding rate at any given time is representative of the number of particles. The binding rate is constant.

In some instances, it may be desirable to repeat the detection of bound particles in order to determine whether the binding rate is constant or whether it has changed over time. Where there are no changes to the binding rate (constant rate), the binding rate recorded at any point is representative of the absolute concentration. Where there are changes to the binding rate, these changes can be plotted and the data extrapolated to a zero time point in order to calculate the concentration.

From a constant binding rate or in case of changes in binding rates from the initial binding rate, the decay or decline in the rate of binding of the particle to the surface can be calculated. The decline in the binding rate can be correlated to the concentration of the particle in the solution. For example, the binding of a particle to the surface (as visualised by iSCAT) decreases over time as a function of the remaining number of particles in solution and accessible sites for binding.

The detection of the binding of the particle to the surface may be repeated over time, and the intervals between measurements will depend upon the nature of the particle and solution which requires measurement, and will vary from solution to solution.

Exemplarily, measurements can be taken addition effectively immediately after the sample has been contacted with the surface, for example within a second or fraction thereof of the contact, and then measurements can be taken every few seconds thereafter, for example with an interval between measurements of 1-60, 1-30, 1-5, 5-10, 10-15, 15-20, 20-25, 25-30, 30-35, 35-40, 45-50, 55-60 seconds after contact. Measurements may be repeated for as long as required in order to determine initial binding rate.

It will be appreciated that the interval between measurements may relate to the particle under investigation, and therefore could be longer, i.e. the time between measurements could be minutes to hours. Therefore, the measurements can be taken every few minutes after the initial measurement, for example with an interval between measurements of 1-60, 1-30, 1-5, 5-10, 10-15, 15-20, 20-25, 25-30, 30-35, 35-40, 45-50, 55-60 minutes after contact. Alternatively or additionally, the measurements can be taken every few hours after the initial measurement, for example with an interval between measurements of 1-24, 1-12, 1-6, 1-5, 1-4, 1-3, 1-2 hours or 1 hour after contact.

Longer intervals are considered to provide further evidence that there is no dissociation within the few minutes of the actual measurement, as it would be possible to show that it takes much longer to occur.

Additionally, the time intervals can be varied within one assay. For example, the first few measurements can be taken every few seconds, and further measurements can be taken with a longer time interval of minutes. So long as the time of detection is recorded, the interval can be varied.

It is preferred that binding is detected at least once subsequent to the initial detection. Preferably, binding of the particle to the surface is detected twice or more, even more preferably three times, four times, five times, six times, seven time, eight times, nine times or more. Each independent detection event of the binding of the particle to the surface is separated by a time interval as discussed previously which can be the same time interval between each detection event, or vary.

In order to detect the binding rate, it may be useful to record/video the binding to the surface, as shown in Example 4.

Determination of Concentration

In order to determine the concentration of the particle in solution, the constant or initial binding rate may be compared to the constant or initial binding rate for a known concentration of the particle in solution. This allows the method to be calibrated, since the method has previously been performed for a particle of known concentration.

Figure 7:
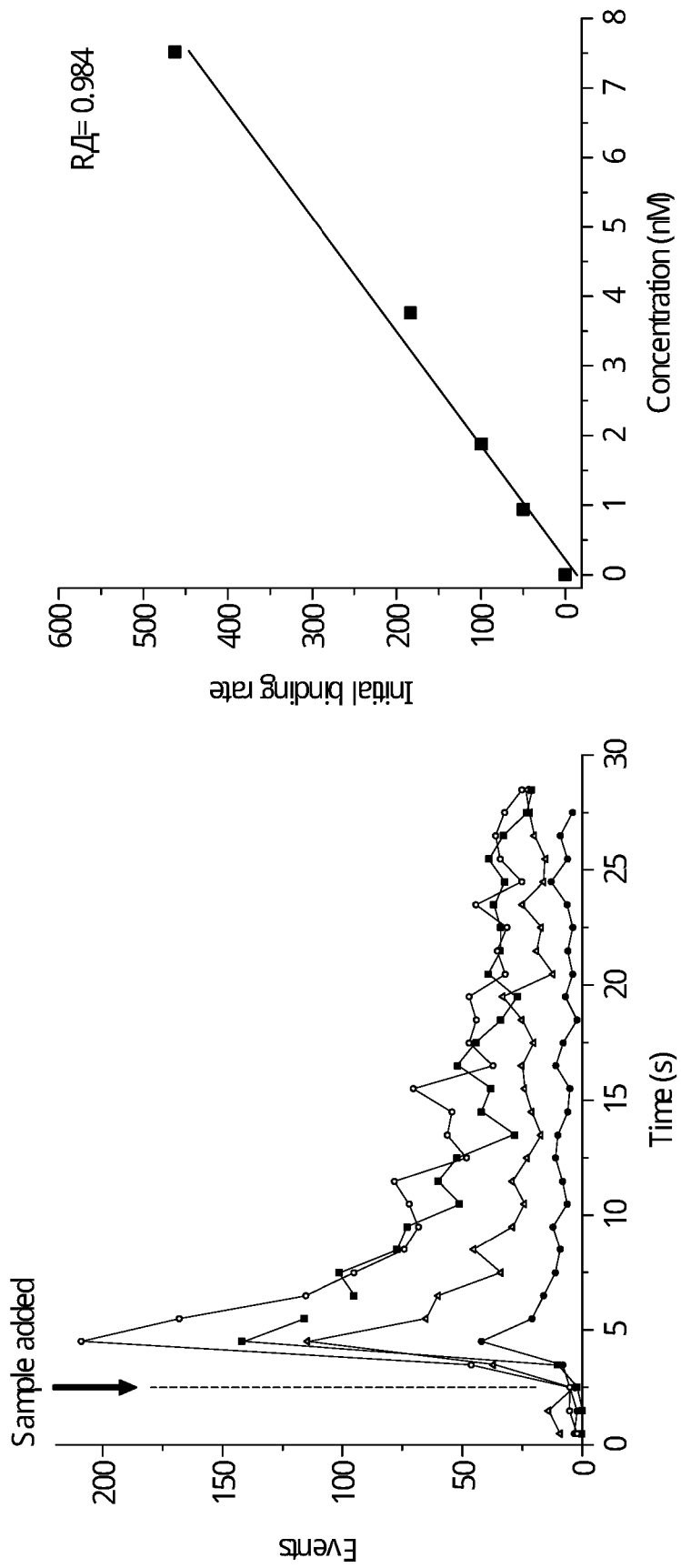
FIG. 7 shows calibration of iSCAT measurements using lipoproteins of known mass/concentration. The left panel plots binding events of particles against incubation time (seconds). The right panel plots initial binding rates determined from the binding data against concentration, to provide a calibration curve allowing for conversion of measured initial binding rate to concentration of particles in the sample.

Initial binding rates for a series of known concentrations may be extrapolated from the binding data and used to generate a standard curve allowing for conversion of a measured initial binding rate in the sample to the respective absolute concentration of the particle. In an embodiment it is possible to calibrate concentration measurements made using light scattering microscopy by using particles of known mass/concentration. An example is shown in FIG. 7, where the particle is a lipoprotein. The left panel plots binding events of particles against incubation time (seconds). The right panel plots initial binding rates determined from the binding data against concentration, to provide a calibration curve allowing for conversion of measured initial binding rate to concentration of particles in the sample. In this instance, the binding rate is the rate of binding of the particle to a surface. This surface is present in the sample holder for this embodiment, in which the solution is held.

Analysis of the decay or decline in the detected binding rate of the particle to a surface over time may provide the basis for enabling measurement of concentration. It may be necessary to use binding rates of known concentrations of the particle in order to calibrate the method.

In order to calculate the concentration, it may be necessary to include correction for diffusion rates. Diffusion rates can be readily calculated based on known properties of the particle, such as mass and shape.

Alternatively, the assay may be calibrated using an internal calibrant. The calibrant has similar characteristics to the particle in respect of ability to bind to the surface (e.g. charge, hydrophobicity, hydrophilicity), and is therefore selected based upon the nature of the particle in solution. The calibrant has a known mass and concentration. The calibrant is introduced to the particle in solution and the surface substantially simultaneously (i.e. at the same time). Detection of the calibrant binding to the surface using light scattering allows for determination of the initial binding rate of the calibrant. Simultaneously, the initial binding rate of the particle to the surface is determined using light scattering. The initial binding rate of the particle can be compared to the initial binding rate of the known concentration of calibrant, which permits calculation of the concentration of the particle.

Single particle light scattering can be used to determine the mass of the particle, as discussed in earlier publications, and it is therefore possible to determine the binding rate of one particular particle type, using mass to identify the particles of interest. The particle of interest or calibrant may be selected using contrast, which is related to the mass. It is therefore possible to detect the binding of only the particle or the calibrant to the surface, and disregard the binding of other solutes to the surface.

Concentrated Solutions

If a solution is suspected of being concentrated, this can make the measurement of concentration more complex. In order to ensure that the measurements determined using the methods of the invention are correct the inventors have developed a method using a measuring solution. This is introduced to the particle solution with the surface, at substantially the same time.

The measuring solution may be a buffering solution. Generally, the volume of the measuring solution is known in order to enable calculation of dilution effects.

A volume of the particle solution may be placed into a sample holder, preferably with a known geometry. This enables the introduction of a volume of a measuring solution (or introduction of the particle solution into the measuring solution), and using dilution behaviour, this allows the detected binding rate of the particle to the surface to be converted to concentration of the particle.

The detection of the binding of the particle to the surface may be taken at one or more different time intervals following the introduction of the measuring solution, as detailed above. If the detection step is repeated after introduction of measuring solution at different time intervals, this will allow for correction for dilution effects, such as dissociation. If the measurements are taken at different time point after addition (and thus dilution) a change in, for example, species distribution if the particle dissociates or clusters at lower concentrations, can be visualised. This approach, therefore, allows a more detailed view of the particle and enables the verification of the concentration measurement.

Alternatively or additionally, the volume of one or both of the solutions (particle or measuring) can be varied, and/or the geometry of the sample holder can be varied. Both allow for correction of dilution effects. If the detection step is repeated in one or more different solution volumes and/or in sample holders of one or more different geometries this can also correct for dilution effects such as dissociation.

Method Steps

As described herein, the invention provides a method for measuring the concentration of particle a solution, the method comprising:
  i) contacting the solution with a surface;
  ii) detecting the particle binding to the surface as visualised by light scattering;
  iii) repeating the detection step and calculating changes in binding rate and/or the initial binding rate over time of the particle to the surface;
  iv) providing a calibration curve of initial binding rate against concentration based on data from solutions of known particle concentration;
  v) using the calibration curve in step (iv) to convert the initial binding rate recorded for the sample in step (iii) to the concentration of the particle in solution.

The method may further involve repeating steps (i) to (ii) using one or more of a sample holder of different geometry or using a different volume of measuring solution in order to verify the determined concentration.

Alternatively, the method invention provides a method for measuring the concentration of particle a solution, the method comprising:
  i) contacting the solution with a surface;
  ii) detecting the particle binding to the surface as visualised by light scattering;
  iii) repeating the detection step and calculating changes in binding rate and/or the constant binding rate over time of the particle to the surface;

iv) providing a calibration curve of constant binding rate against concentration based on data from solutions of known particle concentration;

v) using the calibration curve in step (iv) to convert the constant binding rate recorded for the sample in step (iii) to the concentration of the particle in solution.

The method may further involve repeating steps (i) to (ii) using one or more of a sample holder of different geometry or using a different volume of measuring solution in order to verify the determined concentration.

If an internal calibrant is used in a method of the invention, the invention provides a method for measuring the concentration of particle a solution, the method comprising:

i) contacting the solution with a surface in the presence of a calibrant;

ii) detecting the particle binding to the surface as visualised by light scattering;

iii) simultaneously detecting the calibrant binding to the surface as visualised by light scattering;

iv) repeating the detection steps (ii) and (iii) and calculating the changes in binding rate and/or initial binding rate over time of the particle and the calibrant to the surface;

v) using the binding rates calculated in step (iv) for the calibrant to convert the initial binding rate of the particle calculated in step (iv) to concentration of the particle in solution.

In all variations, it is the detection of the particle binding to the surface that enables the determination of the concentration of that particle in solution. The binding rate of the particle to the surface may be constant, in which case the constant binding rate may be compared to the constant binding rate for the same particle of known concentration. The binding rate may vary, and thus the initial binding rate may be calculated for comparison with the initial binding rate for the same particle of known concentration. As discussed previously, the nature of the sample holder with respect to surface area to volume ratio can alter the concentration calculation.

Lipoprotein Measurements

As discussed above, the method of the invention allows for direct measurement of size and number of one or more lipoprotein particles, and of the ratio of one or more different lipoprotein particles in a sample. The method may comprise determining the number, size or ratio of two or more different types of lipoprotein particles simultaneously or concurrently. The method may comprise determining the total number of lipoprotein particles of a particular class in the sample, such as the total number of HDL and/or LDL lipoprotein particles. The method may comprise determining the number of lipoprotein particles of a particular size in the sample. The method may comprise determining the distribution of sizes for lipoprotein particles of a particular type in the sample. The method preferably comprises determining the ratio of HDL to LDL lipoprotein particles in the sample. The ratio of HDL and/or LDL to one or more other lipoprotein particles in the sample, such as VLDL lipoprotein particles, may also be determined. The relative number of particles of each lipoprotein type or fraction detected may thus be determined.

The method of the invention may comprise obtaining a single particle histogram for one or more lipoprotein particles in the sample, including the number of particles of each different size detected for a given type of lipoprotein particle. Each particle in the sample is thus detected separately, in contrast to previous detection methods characterising bulk total lipoprotein content. The distribution of lipoproteins in a population can thus be detected directly in contrast to previous detection methods relying on algorithms. The method preferably comprises obtaining a single particle histogram for HDL and/or LDL lipoprotein particles.

The method may comprise determining the mass of lipoproteins in the sample. The method may comprise determining absolute concentrations of one or more types of lipoprotein in the sample. The mass and/or concentration of the lipoproteins may be determined by calibration against suitable standards. Thus, a range of lipoproteins of known mass (such as lipid nanodiscs) may be detected by light scattering, such as by iSCAT. Suitable purified lipoprotein preparations are available for example from Lee Biosolutions, as described in the Examples.

A calibration curve with the relationship between lipoprotein mass and iSCAT signal may thus be generated. The iSCAT signal obtained for particles detected in a sample of interest may then be correlated with the calibration curve to identify their mass.

Absolute concentration in solution may be determined by measuring binding events between lipoprotein particles in the sample and a surface, calibrated against those observed with samples of the lipoprotein of known concentrations. For example, the binding of a particle to the surface (as visualised by iSCAT) decreases over time as a function of the remaining number of particles in solution and accessible sites for binding. Initial binding rates for a series of concentrations may be extrapolated from the binding data and used to generate a standard curve allowing for conversion of a measured initial binding rate in the sample to the respective absolute concentration of the lipoprotein. Alternatively, constant binding rate at a given concentration may be determined by constant supply of sample in a flow chamber or by use of a passivated surface such that only transient binding of particles is possible.

Exemplary calibrations for determination of the mass and concentration of HDL and LDL lipoproteins in a sample are described in the Examples. It should be understood that the methods of the invention may also not include any calibration with known standards. Instead, a comparison of particle sizes and distributions may be made with representative particle sizes/distribution for a lipoprotein fraction of interest.

The method may also comprise determining one or more other parameters of lipoprotein particles in the sample. The method may comprise detecting cholesterol, triglyceride and/or apolipoprotein levels in the sample. The levels of these lipoprotein components may be determined by known methods in the art, as discussed below, or alternatively from knowledge of the average numbers of a molecule of a given type in the lipoprotein particle of interest. Thus, the numbers of a lipoprotein particle of a given type as detected by light scattering, such as by iSCAT, may be multiplied by the known average number of molecules of a lipoprotein component of interest in such a lipoprotein particle, to calculate the total level of that component. For example, an LDL or VLDL particle comprises only one apoB protein per particle (and apoB proteins are absent in HDL particles).

The level of a protein of interest in lipoproteins in the sample may be determined by immunoassay, for example an immunoassay for apoB100. The presence of a particular protein in the lipoprotein particles detected may be determined by use of a detectably labelled agent specifically binding said protein. The agent may comprise any suitable detectable label. The agent may be an antibody specifically binding the protein. Preferably, the detectable label allows for detection of the protein simultaneously or concurrently with detection of the particle by light scattering, such as by iSCAT. Preferably, the detectable label is a fluorescent label (and thus for example the agent is a fluorescently labelled antibody) and particles incorporating the protein are detected by fluorescence. The method of the invention may thus comprise detection of lipoprotein particles by light scattering (such as by iSCAT) and by fluorescence.

The method of the invention may also comprise carrying out one or more other lipoprotein detection methods. Other lipoprotein detection methods include polyacrylamide gradient gel electrophoresis (see for example U.S. Pat. No. 5,925,229A), gradient density ultracentrifugation (see for example US20140049775A1), nuclear magnetic resonance (see for example U.S. Pat. No. 5,343,389A), ion-mobility analysis (see for example U.S. Pat. No. 7,259,018B2). The method may further comprise carrying out the standard Friedewald assay to determine one or more of total glyceride (TG); total cholesterol (TC); HDL-cholesterol (HDL-C); and LDL-cholesterol (LDL-C) level. The Friedewald assay requires precipitation of VLDL and LDL to measure LDL-cholesterol level, as calculated by: TC-(HDL-C+TG/5). Limitations of this assay are its limited accuracy when TG>400 mg/ml, or if VLDL TG/Chol ratio deviates from 5:1. Also fasting of the individual from which the sample for lipoprotein measurements is obtained is required.

The results obtained by light scattering (such as by iSCAT) may be compared with results obtained by the other method(s), or the other method(s) may be used to provide additional information. Thus for example, iSCAT may be used to provide information on particle size and number and total concentrations of one or more lipoprotein components may be determined by other methods.

Detection

The detection of particles, including lipoprotein particles according to the claimed methods are carried out using light scattering, preferably using interferometric scattering microscopy (iSCAT). This technique is reviewed for example in Kukura et al., Nature Methods 2009 6:923-935, and in Ortega-Arroyo et al., Physical Chemistry Chemical Physics 2012 14:15625-15636.

iSCAT comprises determining interference between light scattered by an object in a sample and light reflected from the sample location. The interference is dependent on the scattering amplitude of the object (and in turn its volume), and is measured as an iSCAT signal. Thus, the iSCAT signal generated by a lipoprotein particle may be correlated with its volume and diameter to identify the type of lipoprotein particle present in the sample. On calibration, the iSCAT signal may also be used to estimate mass/concentration of particles, as described below. Thus, the method of the invention typically comprises determining an iSCAT signal. The isCAT signal may be described as the ratio of detected light in the presence and absence of a particle. In more detail, it may be defined as $(I_s-I_p)/I_s$, where $I_s$ is the reflected intensity from a sample location (such as a glass surface) in the absence of a particle, and $I_p$ the same measure in the presence of a particle.

The method may comprise use of an interferometric scattering microscope comprising: a sample holder for holding a sample in a sample location; an illumination source arranged to provide illuminating light; a detector; and an optical system being arranged to direct illuminating light onto the sample location and being arranged to collect output light in reflection, the output light comprising both light scattered from the sample location and illuminating light reflected from the sample location, and direct the output light to the detector. The microscope may further comprise a spatial filter positioned to filter the output light, the spatial filter being arranged to pass output light but with a reduction in intensity that is greater within a predetermined numerical aperture than at larger numerical apertures. Such a spatial filter advantageously maximises image contrast, as described in PCT/GB2017/052070, and also in Cole et al (ACS Photonics, 2017, 4(2), pp 211-216), each incorporated by reference herein.

The light used may be: ultraviolet light (which may be defined herein as having wavelengths in the range from 10 nm to 380 nm); visible light (which may be defined herein as having wavelengths in the range from 380 nm to 740 nm); infrared light (which may be defined herein as having wavelengths in the range from 740 nm to 300 μm). The light is preferably visible light. Blue light is preferred for high sensitivity of detection of lipoprotein particles. Red light may also be advantageously used to allow for combining detection of particles by iSCAT with detection of specific lipoprotein components (for example a specific protein of interest) by fluorescence, for example using a fluorescently labelled antibody binding the protein of interest. The light may be a mixture of wavelengths. The illuminating light may be coherent light, provided for example by a laser.

Figure 3:
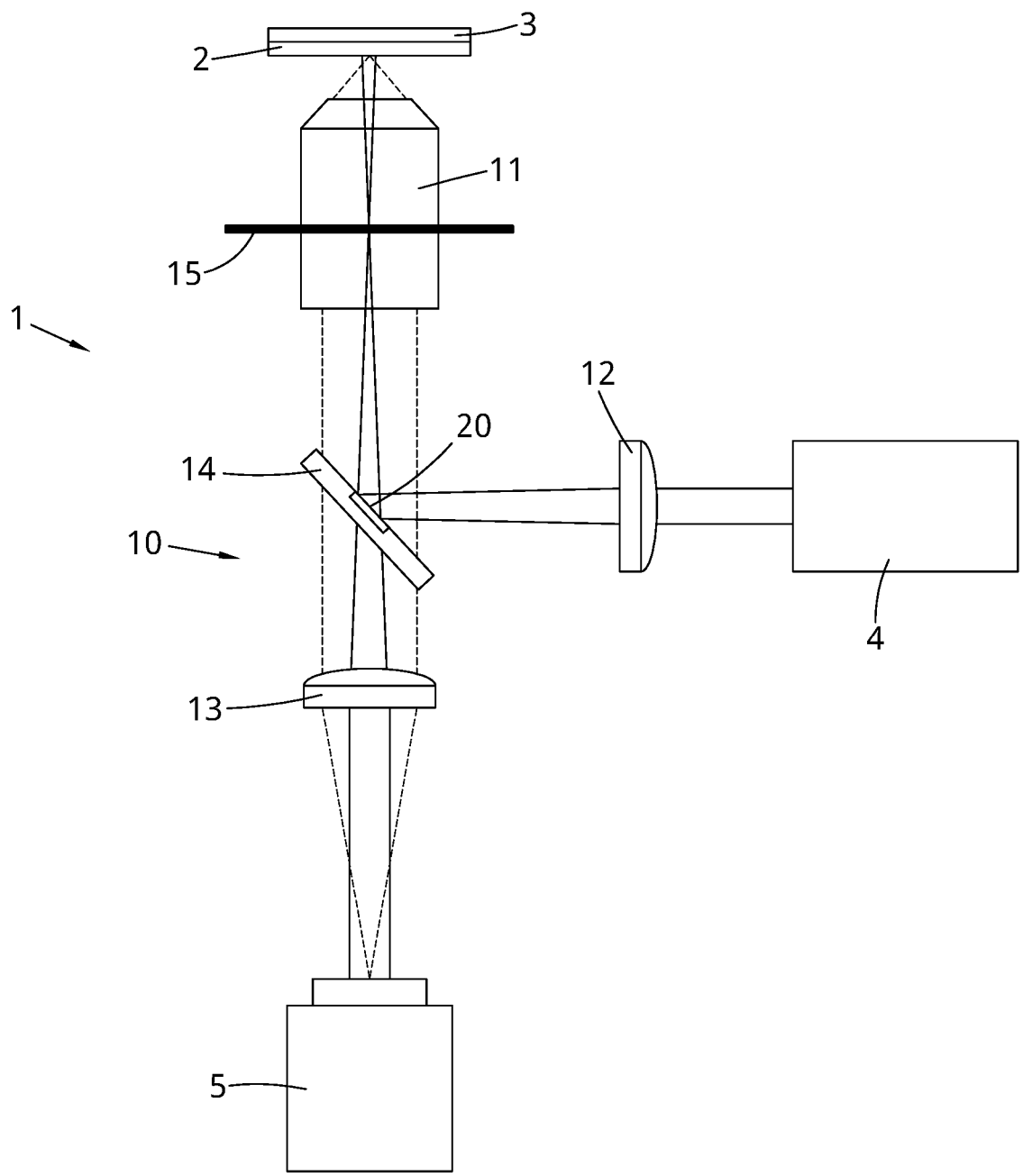
FIG. 3 is a schematic diagram of an iSCAT microscope incorporating a spatial filter.

FIG. 3 illustrates an iSCAT microscope 1 which may be employed in the invention which is arranged as follows (and configured with a spatial filter as discussed above). The spatial filter is advantageous for the reasons discussed, to improve contrast, but the method of the invention may alternatively employ an iSCAT microscope without a spatial filter.

The microscope 1 includes the following components that, except for the spatial filter described in more detail below, have a construction that is conventional in the field of microscopy.

The microscope 1 comprises a sample holder 2 for holding a sample 3 at a sample location. The sample 3 may be a liquid sample comprising objects to be imaged, which are described in more detail below. The sample holder 2 may take any form suitable for holding the sample 3. Typically, the sample holder 2 holds the sample 3 on a surface, which forms an interface between the sample holder 2 and the sample 3. For example, the sample holder 2 may be a coverslip and/or may be made from glass. The sample 3 may be provided on the sample holder 2 in a straightforward manner, for example using a micropipette.

The microscope 1 further comprises an illumination source 4 and a detector 5.

The illumination source 4 is arranged to provide illuminating light. The illuminating light may be coherent light. For example, the illumination source 4 may be a laser. The wavelength of the illuminating light may be selected in dependence on the nature of the sample 3 and/or the properties to be examined. In one example, the illuminating light has a wavelength of 405 nm.

Optionally, the illumination light may be modulated spatially, to remove speckle patterns that arise from the coherent nature of the illumination and laser noise, for example as detailed in Kukura et al., "High-speed nanoscopic tracking of the position and orientation of a single virus", Nature Methods 2009 6:923-935.

The detector 5 receives output light in reflection from the sample location. Typically, the microscope 1 may operate in a wide-field mode, in which case the detector 5 may be an image sensor that captures an image of the sample 3. The microscope 1 may alternatively operate in a confocal mode, in which case the detector 5 may be an image sensor or may be a point-like detector, such as a photo-diode, in which case a scanning arrangement may be used to scan a region of the sample 3 to build up an image. Examples of image sensors that may be employed as the detector 5 include a CMOS (complementary metal-oxide semiconductor) image sensor or a CCD (charge-coupled device).

The microscope 1 further comprises an optical system 10 arranged between the sample holder 2, the illumination source 4 and the detector 5. The optical system 10 is arranged as follows to direct illuminating light onto the sample location for illuminating the sample 3, and to collect output light in reflection from the sample location and to direct the output light to the detector 5.

The optical system 10 includes an objective lens 11 which is a lens system disposed in front of the sample holder 2. The optical system 10 also includes a condenser lens 12 and a tube lens 13.

The condenser lens 12 condenses illuminating light from the light source 11 (shown by continuous lines in FIG. 1) through the objective lens 11 onto the sample 3 at the sample location.

The objective lens 11 collects the output light which comprises both (a) illuminating light reflected from the sample location (shown by continuous lines in FIG. 1), and (b) light scattered from the sample 3 at the sample location (shown by dotted lines in FIG. 1). The reflected light is predominantly reflected from the interface between the sample holder 2 and the sample 3. Typically, this is a relatively weak reflection, for example a glass-water reflection. For example, the intensity of the reflected illuminating light may be of the order of 0.5% of the intensity of the incident illuminating light. The scattered light is scattered by objects in the sample 3.

In a similar manner to conventional iSCAT, scattered light from objects at or close to the surface of the sample constructively interfere with the reflected light and so are visible in the image captured by the detector 5. This effect differs from a microscope operating in transmission wherein the illuminating light that reaches the detector is transmitted through the depth of the sample leading to a much smaller imaging contrast.

As shown in FIG. 1, the reflected illuminating light and the scattered light have different directionalities. In particular, the reflected illuminating light has a numerical aperture resulting from the geometry of the beam of light output by the light source 4 and the optical system 6. The scattered light is scattered over a large range of angles and so fills larger numerical aperture than the reflected illuminating light.

The tube lens 13 focuses the output light from the objective lens 11 onto the detector 5.

The optical system 6 also includes a beam splitter 14 that is arranged to split the optical paths for the illuminating light from the light source 4 and the output light directed to the detector 5. Except for the provision of a spatial filter as described below, the beam splitter 14 may have a conventional construction that provides partial reflection and partial transmission of light incident thereon. For example, the beam splitter 14 may be a plate, typically provided with a film, which may be metallic or dielectric, arranged at 45° to the optical paths. Alternatively, the beam splitter 14 may be a cube beam splitter formed by a matched pair of prisms having a partially reflective film at the interface between the prisms. Alternatively, the beam splitter 14 may be a polarising beam splitter, used in combination with a quarter wave plate between the beam splitter 14 and the sample 3.

In the example shown in FIG. 1, the light source 4 is offset from the optical path of the objective lens 11 so that the illuminating light from the light source 4 is reflected by the beam splitter 14 into the objective lens 11, and conversely the detector 5 is aligned with the optical path of the objective lens 11 so that the output light from the sample location is transmitted through the beam splitter 14 towards the detector 5.

In addition to the components described above that may be of a conventional construction, the microscope 1 includes a spatial filter 20. In the example shown in FIG. 1, the spatial filter 20 is formed on the beam splitter 14 and is thereby positioned behind the back aperture of the objective lens 11, and so directly behind the back focal plane 15 of the objective lens 11. Thus, the spatial filter 20 may be implemented without entering the objective lens as in phase contrast microscopy. Placing the spatial filter directly behind the entrance aperture of the objective rather than in a conjugate plane (for example as described below) has the distinct advantage of strongly suppressing back reflections originating from the numerous lenses within high numerical aperture microscope objectives. This, in turn, reduces imaging noise, lowers non-interferometric background and reduces the experimental complexity, number of optics and optical pathlength leading to increased stability of the optical setup and thus image quality.

However this location is not essential and a spatial filter having an equivalent function may be provided elsewhere as described below.

The spatial filter 20 is thereby positioned to filter the output light passing to the detector 5. In the example shown in FIG. 1 in which the detector 5 is aligned with the optical path of the objective lens 11, the spatial filter 20 is therefore transmissive.

The spatial filter 20 is partially transmissive and therefore passes the output light, which includes the reflected illumination light, but with a reduction in intensity. The spatial filter 20 is also aligned with the optical axis and has a predetermined aperture so that it provides a reduction in intensity within a predetermined numerical aperture. Herein, numerical aperture is defined in its normal manner as being a dimensionless quantity characterising a range of angles with respect to the sample location from which the output light originates. Specifically, the numerical aperture NA may be defined by the equation $NA=n \cdot \sin(\theta)$, where $\theta$ is the half angle of collection and n is the refractive index of the material through which the output light passes (for example the material of the components of the optical system 6).

The spatial filter 20 provides no intensity reduction outside the predetermined numerical aperture. In principle, the spatial filter 20 could alternatively provide a reduction in intensity outside its predetermined aperture, but a reduction in intensity that is less than the reduction in intensity within the predetermined numerical aperture, although this is less desirable.

The spatial filter 20 may be formed in any suitable manner, typically comprising a layer of deposited material. The material may be, for example, a metal such as silver. The deposition may be performed using any suitable technique.

As sub-diffraction sized objects near an interface scatter light preferentially into a larger numerical aperture than the reflected illuminating light, the reduction in intensity provided by the spatial filter 20 preferentially reduces the intensity in detection of the reflected illuminating light over the scattered light. Accordingly, the reduction in intensity by the spatial filter 20 at low numerical apertures predominantly affects the reflected illuminating light and has a minimal effect on the scattered light, thereby maximising the contrast in the capture image. The enhanced imaging contrast enables high contrast detection of objects that are weak scatterers.

The contrast enhancement may be understood as follows. As the spatial filter 20 passes part of the output light in the predetermined numerical aperture (i.e. is partially transmissive in this example), fractions of illuminating light and scattered light fields reach the detector and interfere for a sufficiently coherent illumination source. The light intensity reaching the detector $I_{det}$ is then given by $I_{det}=|E_{inc}|^2\{r^2t^2+|s|^2+2rt|s|\cos\Phi\}$, where $E_{inc}$ is the incident light field, $r^2$ is the reflectivity of the interface and $t^2$ is the transmissivity of the spatial filter 20, s is the scattering amplitude of the object, and $\Phi$ is the phase difference between transmitted illuminating light and the scattered light. Thus, the scattering contrast is enhanced, albeit at the expense of the total number of detected photons.

Thus, contrast is provided in a similar manner to conventional iSCAT, but controlled additionally by the transmissivity of the spatial filter. This provides the ability to tune the amplitude of the reference field directly through selection of the transmissivity $t^2$ of the spatial filter 20 as opposed to being fixed by the reflectivity of a glass-water interface as in standard iSCAT. In the case that the spatial filter 20 is a layer of deposited material, the transmissivity $t^2$ may be selected by choice of the material and/or thickness of the layer. Such tuning may be performed according to, for example, the scattering object of interest, the camera full well capacity and magnification.

To maximise these beneficial effects to iSCAT, the predetermined numerical aperture may be the numerical aperture of the reflected illuminating light within the output light, but that is not essential. For example, benefits of a similar nature could be achieved if the predetermined numerical aperture was slightly smaller than, or larger than the numerical aperture of the reflected illuminating light.

Sample Including Lipoproteins

The sample may be any sample comprising lipoprotein particles. The particles are typically lipoprotein particles produced in vivo, such as in a human or animal. Thus, the lipoprotein particles are typically present in a biological sample. However, lipoprotein particles produced in vitro and/or provided in purified form may also be detected, for example for calibration purposes as discussed above. The sample may comprise multiple different types of lipoproteins in purified form. The sample may also be a complex mixture or polydisperse solution of various components, such as a solution comprising multiple different ions, proteins and lipoproteins.

Where the sample is a biological sample obtained from a human or an animal, it may be a clinical sample. The sample may be a clinical sample from any subject as described below in the context of the methods of treatment and diagnosis of the invention. It may be a sample of any body fluid or tissue comprising lipoprotein particles. Typically, the sample is blood or a component of blood, such as plasma or serum. The sample may be capillary, venous or arterial blood or plasma or serum therefrom. Collection of samples may be performed by any means, including by finger prick or by venipuncture.

As discussed above, the detection of lipoproteins according to the invention is advantageously achieved without separation or purification of lipoproteins from other components of a sample. Such separation and purification as required in previous detection methods is time-consuming and may also artificially change certain properties of lipoprotein particles. However, it should be understood that a biological sample such as blood will typically be diluted in order to reduce density of particles and assist optimal resolution of different types of lipoprotein particles. The sample may be diluted in any suitable buffer. Typically, a suitable buffer has a physiological pH and salt concentration. Non-physiological buffer conditions may also be used to examine effects of these conditions on lipoprotein particles.

The skilled person is able to select an appropriate dilution of a given sample for detection of particular lipoprotein particles of interest by routine experimentation. The dilution may be made empirically until a dilution is identified that allows for detection of single particles, according to the imaging speed and sensitivity of the detection instrument. The dilution factor will then be taken into account to extrapolate to the number of the lipoprotein particles in the undiluted sample.

Where the sample is blood or plasma, it may be diluted 10 000 times or greater in a suitable buffer to allow for detection of HDL (which is relatively dense compared to LDL at high concentration) or for optimal detection of resolution of HDL and LDL at the same time. A lower dilution (1-5000 times) may be used for detection of LDL.

The sample volume required for detection of lipoproteins by iSCAT is minimal, and may be as little as a microlitre, depending on the sample type and means of collection. Finger prick allows for very small volumes of blood to be collected. The sample may be provided in any suitable sample chamber. The sample chamber may be provided by a gasket on a coverslip, for example as described in the Examples. The sample chamber may alternatively be a flow chamber or micro-fluidic device or chip, such as a capillary chip.

Method of Diagnosis or Determining Risk

The invention has particular utility in diagnostic applications, based on the correlation between size, number, distribution and ratio of different types of lipoprotein particles with disease. The invention accordingly provides a method for diagnosing a disease or condition associated with size and/or number of lipoprotein particles in an individual, or for determining the risk that the individual will develop said disease or condition, comprising detecting the size and/or number of lipoprotein particles in a sample from said individual by interferometric scattering microscopy. The detection may be carried out in any way described above in connection with the methods of detection of the invention, and for any type of lipoprotein particle(s) as described above. Thus, the method may comprise detecting the size and/or number of more than one different type of lipoprotein particle, or the ratio of different types of lipoprotein particle, in said sample. The method preferably comprises detecting high density lipoprotein (HDL) particles and/or low density lipoprotein (LDL) particles. The method may particularly comprise determining the ratio of HDL to LDL particles in said sample. The sample may be any biological or clinical sample described above, preferably blood, serum or plasma. The individual may be an animal, mammal or human.

Particular lipoprotein particle levels, distributions and sizes may be correlated with disease. HDL, described in the art as "good cholesterol" functions as the transit for cholesterol away from blood, tissues, and organs of the body towards the liver. Thus, normal HDL levels provide for appropriate regulation of blood cholesterol levels. Changes in HDL level/redistribution of cholesterol to other lipoprotein particles may be associated with disease or increased risk of disease. For example, having HDL cholesterol (concentration of cholesterol carried by HDL particles) levels of less than 40 mg/dL for men and less than 50 mg/dL for women is a major risk factor for heart disease. (Mayo Clinic, 2016). HDL particles are normally the most frequent lipoprotein fraction in blood.

LDL, the next most frequent lipoprotein fraction in normal blood, is in contrast often deemed the "bad cholesterol", due to its role in dispositioning cholesterol to tissues and organs of the body. Having high levels of LDL can lead to plaque formation in the arteries, possibly increasing the risk of heart disease and stroke (American Heart Association, 2014). LDL size has also been shown to be linked to cardiovascular health. Normal LDL cholesterol (concentration of cholesterol carried by LDL particles) level is in the range of 100-129 mg/dL. The smaller the LDL particles, the greater correlation to a cardiovascular event. (Foroutan, MS, RDN, 2015).

Other lipoprotein fractions (VLDL, IDL, UDL) are 10-100 times less frequent than LDL.

Accordingly, accurate measurement of HDL and/or LDL numbers, sizes and ratios (and of similar parameters for other lipoprotein particles), as afforded by detection according to the invention, provides information of diagnostic value for diseases or conditions associated with size and/or number of lipoprotein particles. Measurement of HDL and LDL numbers/sizes in particular is of diagnostic value for cardiovascular disease. A direct homogeneous assay as provided for according to the invention, rather than determining LDL-C values based on the Friedewald calculation may also improve lipoprotein analyses and allow for a more accurate LDL value, especially in regards to patients suffering from hyperlipidemia (Nauck, Warnick, & Rifai, 2002). Also, although determination of total serum cholesterol levels is used routinely as a diagnostic tool, approximately half of patients who suffer from symptomatic coronary artery disease have normal LDL-cholesterol concentrations measured using standard methods. Therefore, there appears to be a hidden risk not detected by conventional clinical laboratory measurements of cholesterol, which is advantageously avoided by direct detection of lipoprotein particle numbers and sizes according to the invention.

The disease or condition to be diagnosed, or for which risk is to be determined, may be any disease or condition associated with size and/or number of lipoprotein particles. The disease or condition may be associated with size and/or number of HDL and/or LDL lipoprotein particles. The disease of condition may be associated with ratio of HDL to LDL lipoprotein particles. The disease or condition may alternatively or additionally be associated with size and/or number of VLDL, IDL and/or UDL lipoprotein particles, or the ratio of VLDL, IDL and/or UDL to HDL and/or LDL. The disease or condition may be associated with abnormal lipoprotein distribution or size.

The disease or condition may be one in which a decreased number of HDL particles is present compared to a normal (control or reference) level. Thus a decreased number of HDL particles as compared with a control sample or reference sample/level, may be indicative that the individual has said disease or condition, or has an increased risk of developing said disease or condition. The disease or condition may comprise a blood HDL cholesterol concentration of less than 40 mg/dL for men or of less than 50 mg/dL for women. A blood HDL cholesterol concentration of 40-50 mg/dL (1.0-1.3 mmol/L) for men or between 50-59 mg/dL (1.3-1.5 mmol/L) for women is associated with average risk of heart disease). Based on many epidemiologic studies, blood HDL cholesterol concentration of 60 mg/dL (1.55 mmol/L) or higher is associated with a less than average risk of heart disease. A normal HDL cholesterol level may more generally be defined as greater than 1 mmol/L.

The disease or condition may alternatively or additionally be one in which an increased number of LDL particles, or an increased number of LDL particles of smaller size, are present compared to a normal level. Thus, an increased number and/or size of LDL particles as compared with a control sample or reference sample/level, is indicative that the individual has said disease or condition, or has an increased risk of developing said disease or condition. The disease or condition may comprise a blood LDL cholesterol concentration of more than 3 mmol/L. If a person has no other risk factors for cardiovascular disease, a blood LDL cholesterol level of less than 100 mg/dL (2.59 mmol/L) can be regarded as optimal; a level of 100-129 mg/dL (2.59-3.34 mmol/L) near optimal/above optimal, and a level of 130-159 mg/dL (3.37-4.12 mmol/L) borderline high.

The ratio of HDL:LDL may be decreased in the disease or condition.

A normal number and/or size for a given lipoprotein particle is determined by reference to a baseline number and/or size for particles of this type in an individual who does not have any condition associated with size and/or number of lipoprotein particles, such as a condition discussed below. Such an individual thus provides a control or reference number and/or size of one or more lipoprotein particle(s) which may be compared with the number and/or size of one or more lipoprotein particle(s) detected by iSCAT in a sample from the individual on which the above diagnostic method is carried out. The control or reference size/number may an average of the values from multiple normal individuals. The individual may have normal total blood cholesterol level, preferably a normal HDL blood cholesterol and LDL blood cholesterol level, as discussed above. A normal (healthy) total blood cholesterol level is below 5 mmol/L.

The method of diagnosis or determining risk of the invention thus typically comprises a step of comparing the number and/or size of one or more lipoprotein particle(s) in the sample from the individual with a control number and/or size for said lipoprotein particle(s). An increased or decreased number and/or size for the lipoprotein particle(s) may be indicative of presence of the disease or condition, or a risk thereof, as discussed further below. It should be understood that the control or reference level may be previously determined by iSCAT or by any other method of detecting lipoprotein particles such as any other known detection method described herein. Alternatively, number and/or size of lipoprotein particles may be detected by iSCAT in a control sample simultaneously cholesterol level or distribution. The individual may have any cholesterol-related condition. The disease or condition may be associated with increased or high levels of total blood cholesterol, HDL cholesterol and/or LDL cholesterol. Normal total cholesterol and HDL and LDL cholesterol levels are discussed above. The disease or condition may be associated with increased or high levels of triglycerides. The disease or condition is preferably a cardiovascular disease. The disease or condition may be a vascular disease.

Cardiovascular disease (CVD) refers to a class of diseases that involve the heart or blood vessels. Cardiovascular diseases involving the blood vessels are also known as vascular diseases. The disease or condition may be any vascular disease. The disease or condition may be selected from any of coronary artery disease, coronary heart disease, ischemic heart disease, peripheral arterial disease, cerebrovascular disease, stroke, mini-stroke, renal artery stenosis, and aortic aneurysm. The disease or condition may be any cardiovascular disease that involves the heart. The disease or condition may be selected from any of hypertensive heart disease, secondary to high blood pressure, hypertension, heart failure, pulmonary heart disease, cardiac dysrhythmias, abnormalities of heart rhythm, inflammatory heart disease, endocarditis, inflammatory cardiomegaly, myocarditis, valvular heart disease, and rheumatic heart disease. The disease or condition may be hypercholesterolemia, such as familial hypercholesterolemia. The disease or condition may be any non-cardiovascular disease or condition associated with increased cholesterol or triglycerides, such that diagnosis of number and/or size of lipoprotein particles may assist in diagnosis (and treatment) of this aspect of the disease or condition. Examples of such diseases and conditions include diabetes, kidney disease, an underactive thyroid, or an inflamed pancreas (pancreatitis).

The individual may be previously characterised as having risk of cardiovascular disease, and/or recommended for a test of blood cholesterol levels. The individual may be previously diagnosed as having a cardiovascular disease, including any of the above diseases. In this aspect, the invention provides for more accurate determination of number and/or size of lipoprotein particles in the individual.

The individual may be selected for diagnosis or assessment of risk based on any risk factor such as gender, age, family history, weight, body mass index, diet or lifestyle. The individual may be over the age of 40; according to NHS Guidelines, people over 40 should have their estimate of CVD risk reviewed regularly. The individual may have a family history of early cardiovascular disease—for example, having a father or brother that developed heart disease or had a heart attack or stroke before the age of 55, or a mother or sister that had such a condition before the age of 65. The individual may have a family member, typically a close family member, who has a cholesterol-related condition, such as familial hypercholesterolaemia. The individual may be overweight or obese. The individual may have high blood pressure or diabetes.

The invention further provides a method of selecting an individual to whom a substance or composition is to be administered, or to whom a regimen is to be prescribed, wherein said substance or composition or regimen is suitable for treating or preventing a disease or condition associated with size and/or number of lipoprotein particles, comprising detecting the size and/or number of lipoprotein particles in a sample from said individual by interferometric scattering microscopy according to the method of detection of the invention, and selecting said patient for said administration or said regimen if the size and/or number of lipoprotein particles detected is indicative of the presence of said disease or condition, or of a risk thereof. The method may comprise additionally selecting the individual based on any risk factor described above.

Suitable substances and compositions for administration are described below. A suitable treatment regimen may comprise a change in lifestyle, diet or exercise.

The invention further provides a kit providing means suitable for use in the methods of detection of lipoprotein particles, or of diagnosing or determining risk, according to the invention. The kit may comprise components suitable for detection of lipoprotein particles by interferometric scattering microscopy. The kit may comprise instructions for use of the kit in accordance with methods of the invention. The instructions may provide reference levels for numbers and sizes of one more lipoprotein particles, and reference single particle histograms for one more lipoprotein particles. The kit may also comprise details regarding which individuals the methods may be carried out upon. The kit may comprise one or more components of a sample chamber, such as a coverslip and gasket, a flow cell, a microfluidic device or a chip, such as a capillary chip. The kit may comprise a means to obtain a sample (typically a blood sample) from the individual, such as a capillary blood collection device, a finger prick collection device, or any instrument comprising a needle. The kit may comprise one or more standard lipoprotein samples (such as nanodisks as described herein) which provide for calibration of measurements of lipoprotein particles according to the invention. The kit may additionally comprise means for the measurement of other laboratory or clinical parameters. Procedures using these kits may be performed by clinical laboratories, experimental laboratories, medical practitioners, or private individuals. The invention further provides use of components suitable for detection of lipoprotein particles by interferometric scattering microscopy in the manufacture of a test kit for diagnosis or determining risk of disease or condition associated with size and/or number of lipoprotein particles. The components may be components of a sample chamber as described above. The test kit may comprise instructions, means or standard samples as described above.

Methods of Treatment and Medical Uses

The invention further provides a method of treating or preventing a disease or condition associated with size and/or number of lipoprotein particles in an individual, the method comprising selecting said individual, or diagnosing or determining risk of said disease or condition in said individual by a method as described above, and administering a substance or composition to the individual, or carrying out a regimen thereon, which is effective to treat or prevent said disease or condition in the individual.

The invention also provides a substance or composition for use in a method of treating or preventing a disease or condition associated with size and/or number of lipoprotein particles in an individual, wherein said individual is diagnosed or determined at risk or selected by a method of the invention as described above.

The invention additionally provides use of a substance or composition in the manufacture of a medicament for treatment of prevention of a disease or condition associated with size and/or number of lipoprotein particles in an individual, wherein said individual is diagnosed or determined at risk or selected by a method of the invention as described above.

The individual may be any individual described above, preferably a human individual. The individual may have or be at risk of any disease or condition described above, and have any risk factor described above. Preferably, the individual may have or be at risk of a cardiovascular disease, which may be any specific cardiovascular disease described above.

The substance or composition is administered in an amount effective for prevention or treatment of said disease. A regimen (such as change in lifestyle, diet or exercise) is typically carried out for a period effective for prevention or treatment of said disease. A suitable regimen may include weight loss, reduction or cessation of smoking or alcohol intake, increased exercise, and/or a healthy diet. The regimen may also comprise surgery, such as a coronary angioplasty or coronary artery bypass. The surgery may comprise introduction of a stent. The prevention or treatment of the disease may be determined by reference to prevention or delay in onset of the disease or by reduction or elimination of one or more symptoms of the disease. The prevention or treatment may induce or prolong remission or delay relapse or recurrence of the disease or condition. The administration of an effective amount or carrying out of an effective regimen may be determined by measurement of a normal lipoprotein particle number, size or ratio in a sample from the individual (or a shift towards normal lipoprotein particle number, size or ratio) following the administration or regimen.

The substance or composition may be any substance or composition suitable for treating or preventing a disease or condition associated with size and/or number of lipoprotein particles, by any means. The substance or composition may reduce LDL concentration or reduce size of LDL lipoprotein particles. The substance or composition may increase HDL concentration. The substance or composition may reduce blood cholesterol levels, including total blood cholesterol levels, or total LDL blood cholesterol levels. The substance or composition may reduce blood pressure or widen arteries. The agent may be a vasodilator. The substance or composition may comprise any known agent for prevention or treatment of cardiovascular disease or reduction of blood pressure. The agent may be a statin. Statins (also known as HMG-CoA reductase inhibitors) are a group of medicines that are able to lower the level of LDL cholesterol in the blood, and which have been found to reduce cardiovascular disease and mortality in those who are at high risk. The agent may be a beta-blocker, nitrate, an ACE (angiotensin-converting enzyme) or angiotensin receptor II inhibitor, a calcium channel blocker or a diuretic.

The substance or composition may be a small molecule inhibitor, a peptide, a protein, an antibody, a polynucleotide, an oligonucleotide, an antisense RNA, small interfering RNA (siRNA) or small hairpin RNA (shRNA).

A polynucleotide, such as a nucleic acid, is a polymer comprising two or more nucleotides. The nucleotides can be naturally occurring or artificial. A nucleotide typically contains a nucleobase, a sugar and at least one linking group, such as a phosphate, 2'O-methyl, 2' methoxy-ethyl, phosphoramidate, methylphosphonate or phosphorothioate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide may be any nucleotide or modified nucleotide, typically a ribonucleotide or deoxyribonucleotide or a modified version thereof. The nucleotide typically contains a monophosphate, diphosphate or triphosphate. Phosphates may be attached on the 5' or 3' side of a nucleotide. The polynucleotide can be a nucleic acid, such as deoxyribonucleic acid (DNA) or a ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains. The polynucleotide may be single stranded or double stranded.

The polynucleotide sequence may be cloned into any suitable expression vector. In an expression vector, the polynucleotide sequence encoding a construct is typically operably linked to a control sequence which is capable of providing for the expression of the coding sequence by the host cell. Such expression vectors can be used to express a construct. Antisense and RNA interference (RNAi) technology for knocking down protein expression are well known in the art and standard methods can be employed to knock down expression of a molecule of interest. Both antisense and siRNA technology interfere with mRNA. Antisense oligonucleotides interfere with mRNA by binding to (hybridising with) a section of the mRNA. RNAi involves the use of double-stranded RNA, such small interfering RNA (siRNA) or small hairpin RNA (shRNA), which can bind to the mRNA and inhibit protein expression.

An oligonucleotide "specifically hybridises" to a target sequence when it hybridises with preferential or high affinity to the target sequence but does not substantially hybridise, does not hybridise or hybridises with only low affinity to other sequences. Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). The hybridisation conditions may be stringent conditions as described in the art.

An antibody may specifically binds to any target molecule (typically a protein). The target molecule may be a component of a lipoprotein particle, such as an apolipoprotein. An antibody "specifically binds" to a protein when it binds with preferential or high affinity to that protein but does not substantially bind, does not bind or binds with only low affinity to other proteins. For instance, an antibody "specifically binds" a target molecule when it binds with preferential or high affinity to that target but does not substantially bind, does not bind or binds with only low affinity to other human proteins.

An antibody binds with preferential or high affinity if it binds with a $K_d$ of $1\times10^{-7}$ M or less, more preferably $5\times10^{-8}$ M or less, more preferably $1\times10^{-8}$ M or less or more preferably $5\times10^{-9}$ M or less. An antibody binds with low affinity if it binds with a $K_d$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The antibody may be, for example, a monoclonal antibody, a polyclonal antibody, a single chain antibody, a chimeric antibody, a bispecific antibody, a CDR-grafted antibody or a humanized antibody. The antibody may be an intact immunoglobulin molecule or a fragment thereof such as a Fab, F(ab')$_2$ or Fv fragment.

Specific routes, dosages and methods of administration of the therapeutic agents described herein may be routinely determined by the medical practitioner.

The agents for use in the methods of treatment described herein may be formulated in pharmaceutical compositions. These compositions may comprise, in addition to the therapeutically active ingredient(s), a pharmaceutically acceptable excipient, carrier, diluent, buffer, stabiliser or other materials well known to those skilled in the art. Such materials should be non-toxic and should not interfere with the efficacy of the active ingredient. The pharmaceutical carrier or diluent may be, for example, an isotonic solution.

The precise nature of the carrier or other material may depend on the route of administration, e.g. oral, intravenous, cutaneous or subcutaneous, nasal, intramuscular and intraperitoneal routes. Examples of suitable compositions and methods of administration are provided in Esseku and Adeyeye (2011) and Van den Mooter G. (2006). For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to an individual may be provided with an enteric coating comprising, for example, Eudragit "S", Eudragit "L", cellulose acetate, cellulose acetate phthalate or hydroxypropylmethyl cellulose.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

The dose may be determined according to various parameters, especially according to the substance used; the age, weight and condition of the individual to be treated; the route of administration; and the required regimen. A physician will be able to determine the required route of administration and dosage for any particular individual. A typical daily dose is from about 0.1 to 50 mg per kg of body weight dependent on the conditions mentioned above. The dose may be provided as a single dose or may be provided as multiple doses, for example taken at regular intervals, for example 2, 3 or 4 doses administered hourly.

Examples of the techniques and protocols mentioned above can be found in Remington's Pharmaceutical Sciences, 20th Edition, 2000, pub. Lippincott, Williams & Wilkins.

A substance or composition used in the above methods and medical uses may be administered alone or in combination with other therapeutic substances, compositions or treatments, for example as adjunct therapy. The other therapeutic compositions or treatments may be administered either simultaneously or sequentially with the substance or composition or treatment of the invention.

EXAMPLES

Example 1—Detection of Purified Lipoprotein Particles by iSCAT

Materials/Methods
Substrate Preparation and Measurement
Borosilicate glass coverslips (No 1.5, 24×50 mm, VWR) were cleaned by sequential rinsing with MilliQ water, followed by ethanol and again MilliQ water. They were then dried under a stream of dry nitrogen. CultureWell silicone gaskets (Grace Bio-Labs) were cut and placed onto the freshly cleaned coverslip providing four independent 30-50 µl sample chambers on the same substrate.
Purified HDL and LDL samples were obtained from Lee Biosystems (LDL cat #360-10; HDL cat #361-10), as described for example at: https://www.leebio.com/product/984/low-density-lipoprotein-ldl-human-serum-360-10.
HDL and LDL were separated by ultracentrifugation. The samples were diluted 500 000 and 50 000 times, respectively.

Data acquisition and analysis was then carried out by iSCAT, with non-specific binding of lipoproteins to the glass substrate being imaged and recorded. The experimental setup was identical to that described in FIG. 4 by Cole et al supra. The images were acquired over 30 seconds (at 100 frame/s) and consisted of 512×512 pixels with a pixel size of 23.4 nm. The images were pixel-binned 3×3 prior to saving, giving a final pixel size of 70.2 nm.
Ratiometric image stacks were generated from the raw movie as described in Cole et al. Particles landing on glass surface were identified in the ratiometric images by an automated spot detection routine based on 2D Gaussian fitting of the point spread function.

Figure 4:
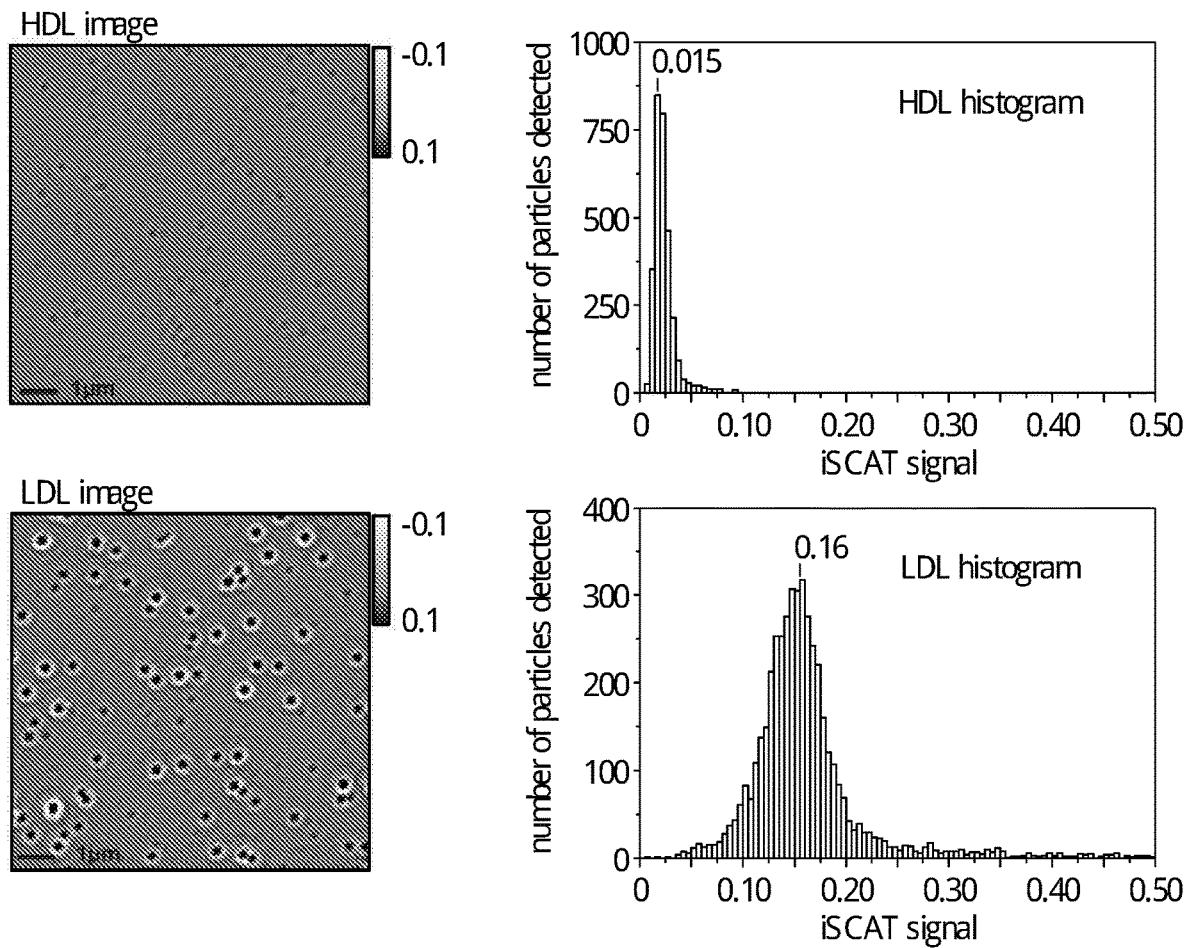
FIG. 4 shows captured images of HDL and LDL lipoprotein particles from purified lipoprotein samples, with the scale bar showing the iSCAT signal, defined as $(I_s-I_p)/I_s$, where $I_s$ is the reflected intensity from the glass surface in the absence of a particle, and $I_p$ the same measure in the presence of a particle. Images of HDL and LDL lipoprotein particles are shown together with single particle histograms obtained from all HDL and LDL images, plotting iSCAT signal against numbers of each particle detected.

Results are shown in FIG. 4, providing images of HDL and LDL detected by iSCAT and corresponding histograms obtained from full series of images.

Example 2—Detection of Purified Lipoprotein Particles from Blood and Serum by iSCAT An iSCAT method as described in Example 1 was carried out on serum and blood samples from a human individual. To obtain blood serum, blood was allowed to clot in an upright position for at least 30 minutes, prior to centrifugation (30 minutes, 1500×g). Serum was transferred to a plastic screw-cap vial. Blood and serum samples were prepared as follows: 1 µl of finger prick blood or serum sample was diluted 2 000 times in HEPES/KCl buffer containing 5 mM EDTA (to prevent clotting) (see below). 10 µl of the diluted sample was added into 40 µl of 25 mM HEPES buffer pH 7.4, containing 100 mM KCl, resulting in a final 10 000 times dilution of blood.

Figure 5:
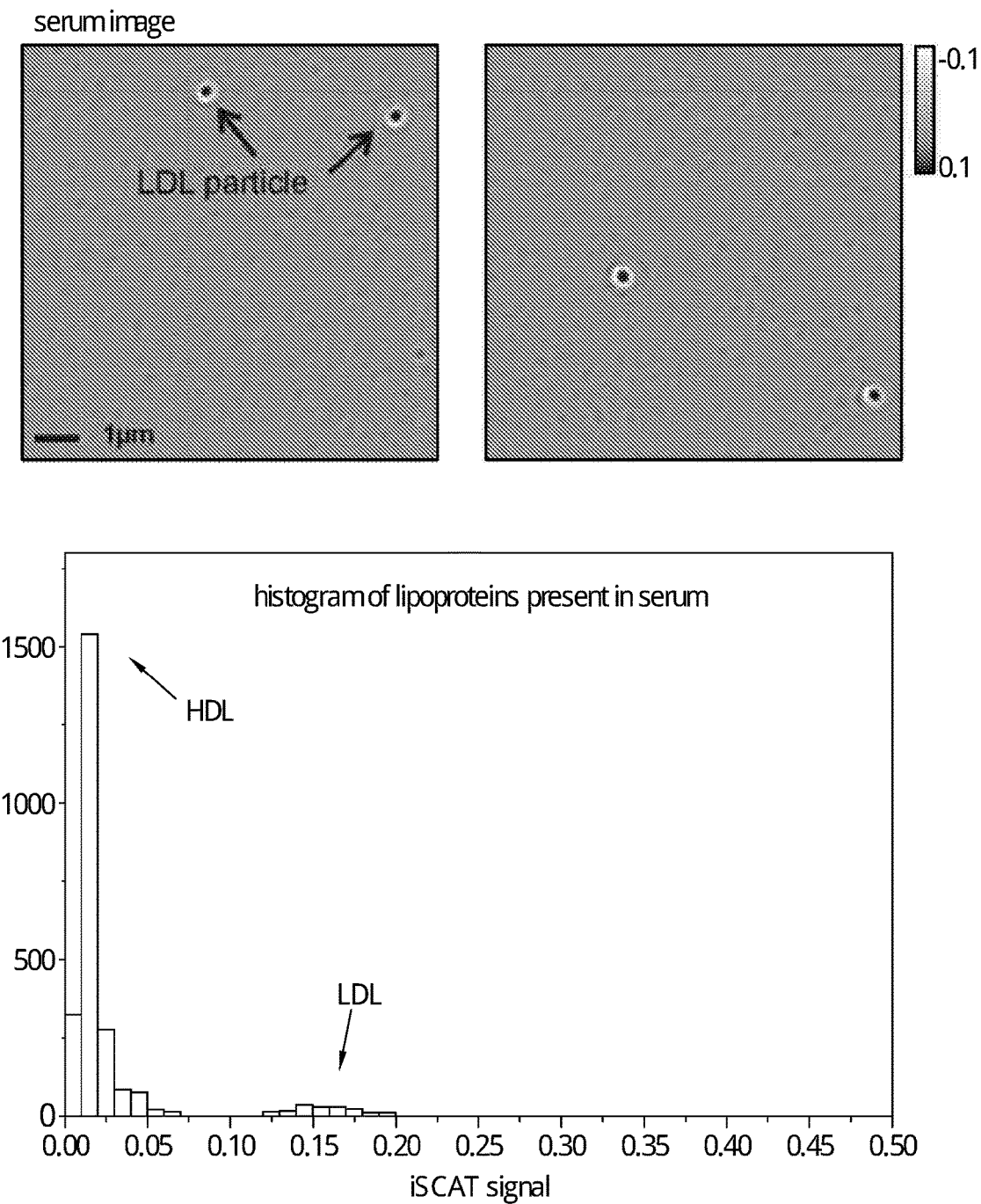
FIG. 5 provides corresponding images and single particle histograms to those shown in FIG. 4 for HDL and LDL lipoproteins detected by iSCAT from a serum sample.

FIG. 5 shows detection of HDL and LDL in a plasma sample. Imaging plasma sample revealed both signals corresponding to HDL and LDL simultaneously. As expected HDL particles were more frequent than LDL (see histogram below).

Figure 6A:
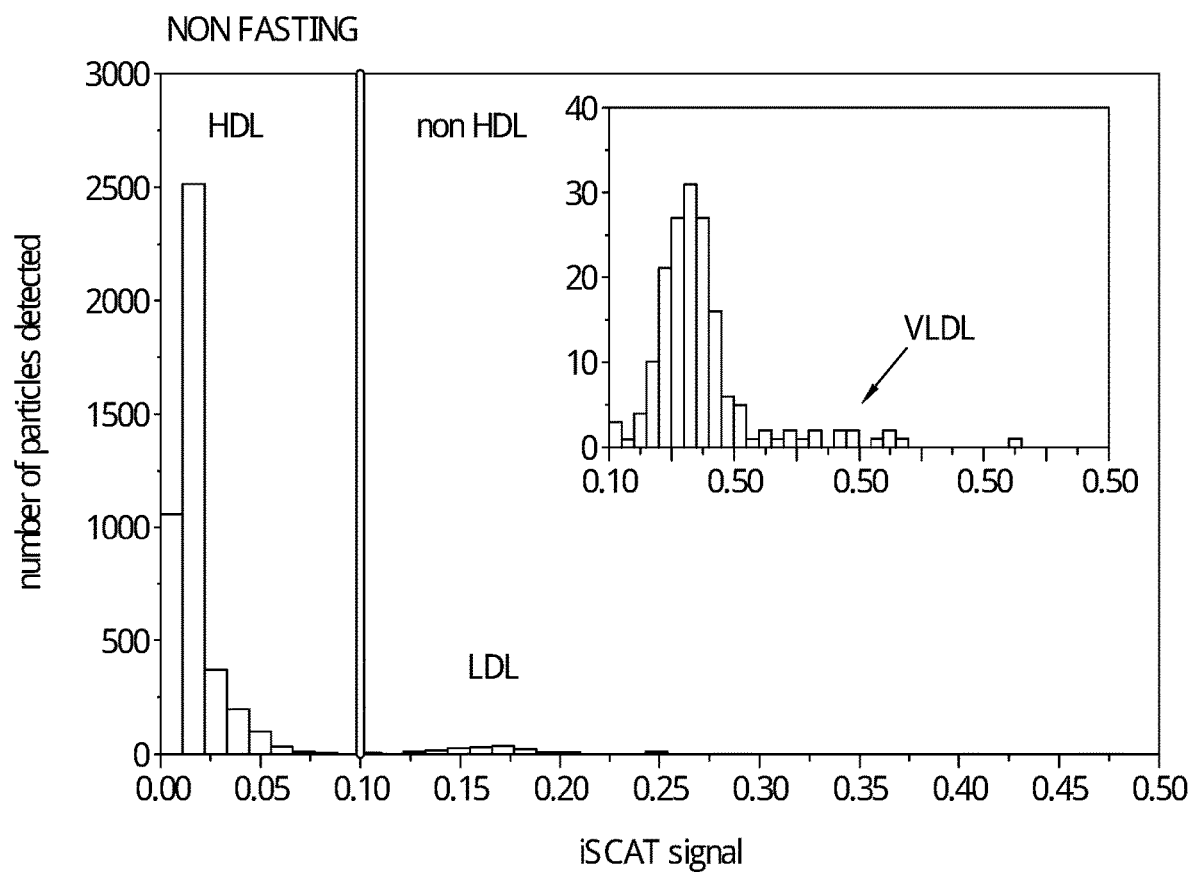
FIGS. 6A and 6B provides histograms from a non-fasting sample and a fasting sample respectively.
Figure 6B:
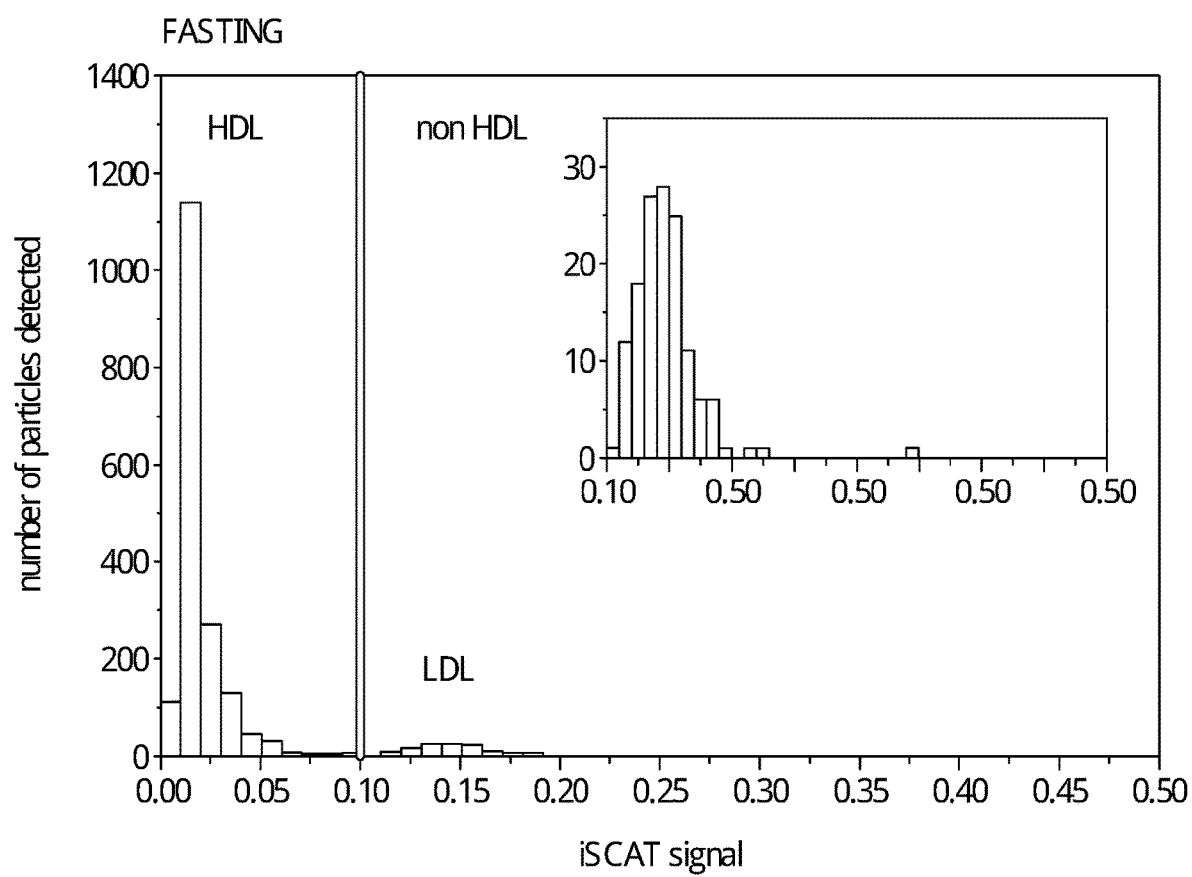

FIGS. 6A and 6B show detection of HDL and LDL in whole blood, with similar results to FIG. 5. We also used both a "fasting sample" and sample collected after a meal. The difference between fasting/non fasting conditions can be noticed in the higher iSCAT signal regime (inserts), which corresponds to larger lipoproteins such as VLDL. As expected these appear after a meal. As discussed previously, the existence of the VLDL fraction is the main reason why patients must fast before standard cholesterol test. VLDLs contain cholesterol, but mainly triglycerides (TG), and if TG levels are too high the standard (Friedewald) method cannot be used. Thus, detection of lipoproteins (including HDL, LDL and VLDL) is possible according to the invention without any requirement for fasting in the individual providing the sample.

Example 3—Calibration to Calculate HDL and LDL Concentrations

To allow for calculation of the mass/concentration of HDL and LDL in the blood samples of Example 2, we established a calibration curve where proteins of known mass/concentration were measured giving a linear relation between molecular weight and iSCAT contrast.

For concentration calibration, we used MSP1D1 DMPC lipid nanodiscs of known concentration. The nanodiscs are synthetic model membrane systems composed of a lipid bilayer of phospholipids with the hydrophobic edge screened by two amphipathic proteins. These proteins are called membrane scaffolding proteins (MSP) and align in double belt formation. The nanodiscs sample was diluted down to the nM range and added to the buffer. Non-specific binding of the nanodiscs to glass was recorded using iSCAT, with Results shown in FIG. 7. The frequency of binding drops as the number of particles in solutions decreases as well as number of accessible sites for binding (as shown in the Left Figure: number binding events as function of time for 4 different concentrations). We fitted the exponential decay and knowing when the sample was added (t=0) extrapolated the initial binding rate.

The initial binding rates were then plotted as function of concentration (Right figure). The slope of the linear fit is the conversion factor, which can be used to determine absolute concentration of a sample using the following relation:

[sample concentration]=[measured initial rate]/[conversion factor]×[sample dilution]

Using this calibration curve, HDL and LDL lipoprotein particle concentration was calculated from whole blood samples in preliminary experiments and found to correlate with expected values.

Example 4—Concentration Measurement for Actin Solution

Generic steps undertaken in calculating the concentration for this Example:
1. Add the sample to the sample holder, which is a high surface-to-volume chamber
2. Start recording individual binding events at a fixed and well-controlled time delay after the sample was applied as indicated on FIG. 7.
3. Compute the frequency of binding as a function of time after addition of the sample
4. Fit the observed decay in binding frequency as a function of time to a single exponential decay function
5. Extract the time zero intercept to determine the binding frequency upon addition of the sample.
6. Repeat the procedure as a function of sample concentration
7. Fit the observed initial binding frequency vs sample concentration to obtain a linear correlation.

Once that correlation is established, for any given sample, the concentration can be estimated by repeating steps 1-5 and establishing the initial binding frequency, which can be converted into a sample concentration from the relation in step 7.

The slope of the linear fit is the conversion factor, which can be used to determine absolute concentration of a sample using the following relation:

[sample concentration]=[measured initial rate]/[conversion factor]×[sample dilution]

Figure 8A:
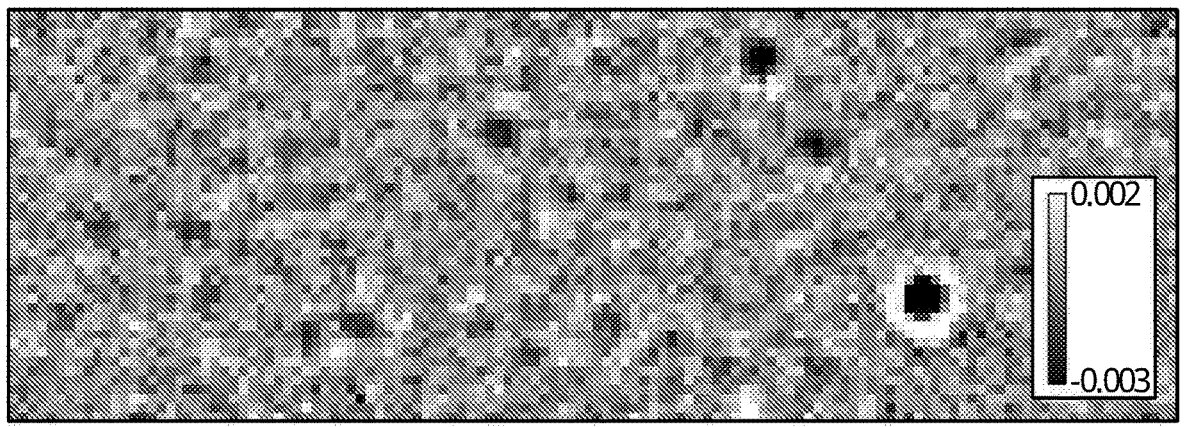
FIG. 8a shows an example frame of landing video of 300 nM actin in gasket with dilution method described in Example 4, recorded at a frame rate of 1 kHz, effective frame rate: 25 Hz.
Figure 8B:
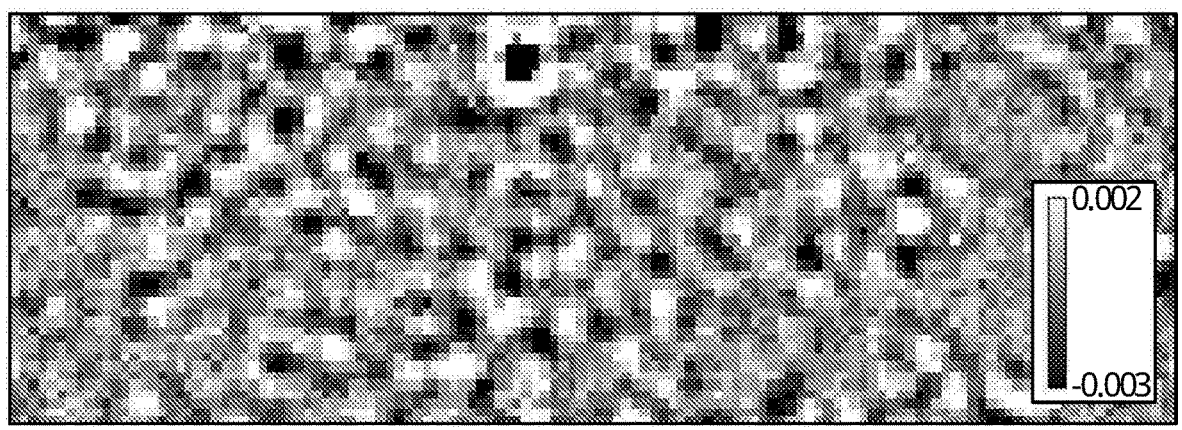
FIG. 8b for comparison with FIG. 8a, FIG. 8b shows an example frame of landing video of 300 nM actin in flow chamber under similar conditions, recorded at a frame rate of 1 kHz, effective frame rate: 25 Hz.

Protocol for Drop Dilution Method on Actin:
   Prepared (3-aminopropyl)triethoxysilane (APTES) coated coverslips as described elsewhere (these coverslips are specific for actin, other proteins would use simple, untreated cleaned glass)
   Cut out 2×2 holes of 3 mm diameter PDMS gaskets (Grace Bio-Labs GBL103250, available through Sigma Aldrich) with a clean scalpel
   Rinsed gaskets with milliQ (MQ) water, isopropanol, MQ water, isopropanol, MQ water and blow-dried with a stream of nitrogen
   Attached gaskets to the centre of an APTES coated coverslip (contact of the PDMS with the glass surface is enough for getting it attached)
   On the microscope, added a 37 ul drop of F-actin buffer to one of the gaskets on the APTES coverslip and adjusted the focus position to the glass surface in that buffer-filled gasket
   Diluted an 11.4 uM stock solution of actin (42 kDa protein that polymerises into filaments) to 333.33 nM in G-actin buffer
   Mixed 90 ul of the 333.33 nM actin stock with 10 ul of a 10× concentrate of F-actin buffer (meant to start polymerisation, specific to actin experiment)→300 nM final actin concentration
   After 15 min of polymerisation, took a 3 ul aliquot out from the 300 nM actin solution with a pipette, pushed it out and created a small droplet at the tip of the pipette, then fused the actin droplet with the drop of buffer in the gasket
   Started recording the landing molecules immediately after perturbations are gone for 1 min
   This method works well for systems where the oligomerisation equilibrium changes slowly compared to the time it takes to dilute the sample and record the video.
Buffers
   G-actin buffer
   2 mM Tris(hydroxymethyl)aminomethane (Tris base)
   0.2 mM $CaCl_2$
   0.2 mM Adenosine triphosphate (ATP)
   2 mM Dithiothreitol (DTT)
   Adjusted to pH 8.0 with HCl
F-Actin Buffer
   10 mM 4-(2-hydroxyethyl)-1-piperazineethanesulfonic acid (HEPES)
   100 mM KCl
   2 mM $MgCl_2$
   1 mM Ethylene glycol-bis(β-aminoethyl ether)-N,N,N', N'-tetraacetic acid (EGTA)
   Adjusted to pH 7.5 with KOH
   Results are shown in FIGS. 8A and 8B. 8A shows an example frame of landing video of 300 nM actin in gasket with dilution method described above, recorded at a frame rate of 1 kHz, effective frame rate: 25 Hz. For comparison, example frame of landing video of 300 nM actin in flow chamber under similar conditions, recorded at a frame rate of 1 kHz, effective frame rate: 25 Hz is shown as 8B.

Figure 9:
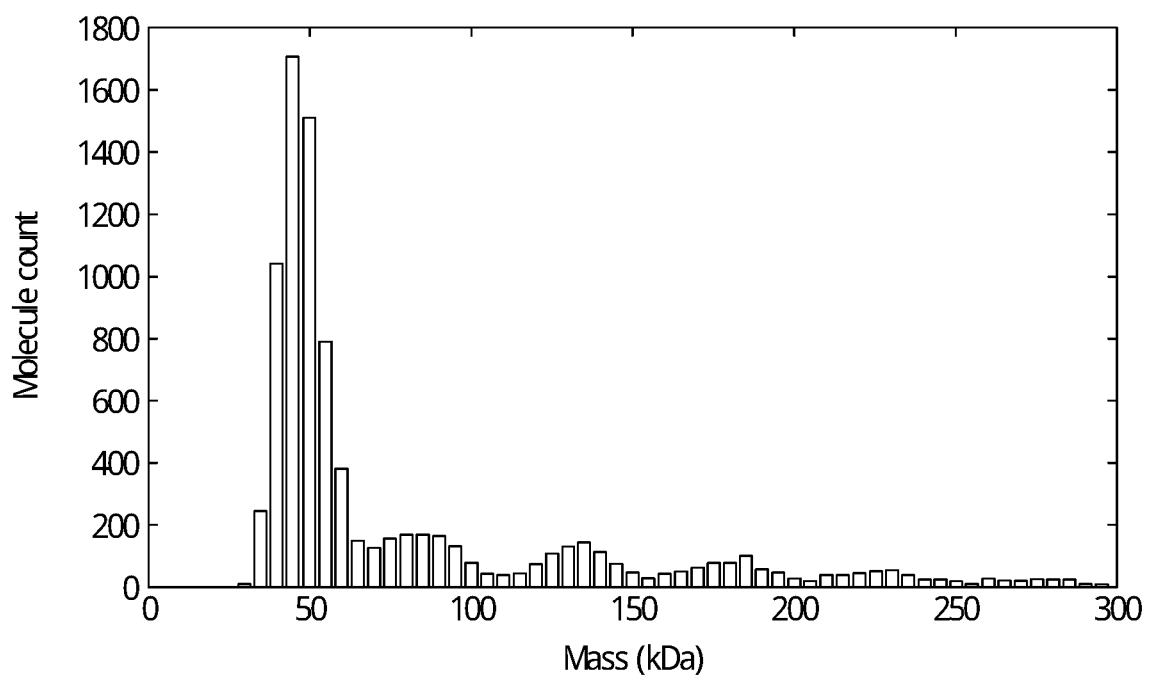
FIG. 9 shows the resulting mass histogram accumulated from 4 repeats of the experiment described in Example 4.

The experiment was repeated 4 times and the resulting mass histogram accumulated is depicted as FIG. 9.

The invention claimed is:

1. A method of measuring the concentration of a particle in a sample, comprising directly contacting the sample with a surface and detecting the non-specific binding of said particle to the surface using single particle interferometric light scattering, wherein the binding rate of the particle to the surface is determined from detecting the binding of the particle.

2. A method as claimed in claim 1, wherein said surface is passivated, activated, coated, treated or derivatized.

3. A method as claimed in claim 1, wherein the detection of binding of the particle to the surface is repeated after one or more time intervals.

4. A method as claimed in claim 3, wherein the repeated detection of binding of said particles to the surface permits calculation of the initial rate of binding of the particle to the surface.

5. A method as claimed in claim 4, wherein the initial binding rate of the particle is compared to the initial binding rate of a known concentration of the particle.

6. A method as claimed in claim 1 wherein the detection of binding of said particles to the surface permits calculation of the constant binding rate of the particle.

7. A method as claimed in claim 6 wherein the constant binding rate of the particle is compared to the constant binding rate for a known concentration of the particle.

8. A method as claimed in claim 1, for measuring the concentration of particle a sample, said method comprising:
   i) contacting the sample with a surface;
   ii) detecting the non-specific particle binding to the surface as visualized by single particle interferometric light scattering;
   iii) repeating the detection step and calculating the changes in initial binding rate over time of the particle to the surface;
   iv) providing a calibration curve of initial binding rate against concentration based on data from solutions of known particle concentration;
   v) using the calibration curve in step (iv) to convert the initial binding rate recorded for the solution in step (iii) to the concentration of the particle in solution.

9. The method as claimed in claim 1, wherein the concentration is absolute concentration.

10. The method as claimed in claim 1, wherein said particle is also contacted with a measuring solution.

11. The method as claimed in claim 1, wherein said sample is contacted with said surface in the presence of a calibrant and the binding of said calibrant to said surface is detected using single particle interferometric light scattering.

12. The method as claimed in claim 11 wherein the binding rate of the calibrant is compared to the binding rate of said particle.

13. The method as claimed in claim 11 wherein the concentration of the calibrant is known.

14. The method of claim 1, wherein said sample is a biological sample.

15. The method as claimed in claim 14 wherein said sample or biological sample is obtained from a human individual.

16. The method as claimed in claim 14 wherein said biological sample is blood, plasma, or serum.

17. A method as claimed in claim 1 wherein the binding rate is determined by a single detection of binding of particles to the surface.

18. The method as claimed in claim 1, wherein said particle is not labelled.

19. The method of claim 1 wherein the mass of the particle is determined by single particle interferometric light scattering, and said mass permits identification of the particle.

20. The method of claim 1 wherein said method comprises the use of an interferometric scattering microscope comprising:
   a sample holder for holding a sample in a sample location;
   an illumination source arranged to provide illuminating light;
   a detector;
   an optical system being arranged to direct illuminating light onto the sample location and being arranged to collect output light in reflection, the output light comprising both light scattered from the sample location and illuminating light reflected from the sample location, and direct the output light to the detector; and a spatial filter positioned to filter the output light, the spatial filter being arranged to pass output light but with a reduction in intensity that is greater within a predetermined numerical aperture than at larger numerical apertures.

21. The method of claim 1 wherein said surface is glass, sapphire or made from transparent polymer.

* * * * *